(12) United States Patent
Field et al.

(10) Patent No.: US 12,718,912 B2
(45) Date of Patent: Aug. 25, 2026

(54) AUTOMATIC SAMPLE AND STANDARD PREPARATION BASED ON RECOGNITION OF SAMPLE IDENTITY AND SAMPLE TYPE

(71) Applicant: Elemental Scientific, Inc., Omaha, NE (US)

(72) Inventors: Michael P. Field, Papillion, NE (US); Daniel R. Wiederin, Omaha, NE (US); Guosheng Zhang, Omaha, NE (US); Kevin Hahn, Urbandale, IA (US); Liang Zhang, Omaha, NE (US); Michael Le, Omaha, NE (US); Karl Hauke, Warranwood (AU)

(73) Assignee: Elemental Scientific, Inc., Omaha, NE (US)

( * ) Notice: Subject to any disclaimer, the term of this patent is extended or adjusted under 35 U.S.C. 154(b) by 1304 days.

(21) Appl. No.: 16/586,029

(22) Filed: Sep. 27, 2019

(65) Prior Publication Data

US 2020/0105383 A1 Apr. 2, 2020

Related U.S. Application Data

(60) Provisional application No. 62/738,527, filed on Sep. 28, 2018.

(51) Int. Cl.
*G16H 10/40* (2018.01)
*G01N 35/00* (2006.01)

(52) U.S. Cl.
CPC ....... *G16H 10/40* (2018.01); *G01N 35/00732* (2013.01); *G01N 35/00871* (2013.01);
(Continued)

(58) Field of Classification Search
None
See application file for complete search history.

(56) References Cited

U.S. PATENT DOCUMENTS 9,523,700 B1 12/2016 Yost et al.
2004/0142486 A1* 7/2004 Weselak .................. G01N 1/00 436/174

(Continued)

FOREIGN PATENT DOCUMENTS

CN 1234869 A 11/1999
CN 108430636 A 8/2018

(Continued)

OTHER PUBLICATIONS https://www.illumina.com/informatics/sample-experiment-management/lims.html (accessed Sep. 25, 2019).

(Continued)

*Primary Examiner* — G. Steven Vanni
*Assistant Examiner* — Meredith Abbott Vassell
(74) *Attorney, Agent, or Firm* — Kevin E. West; Advent, LLP

(57) ABSTRACT

Systems and methods for managing a sample preparation and analysis system based on detected unique sample identities and locations is described. A system embodiment includes, but is not limited to, a sample analysis information system communicatively connected with each of a sample data manager, a sample logging manager, and a sample preparation system, wherein the sample data manager stores on the sample analysis information system a sample type with a sample type protocol for execution by the sample preparation system, the sample logging manager assigns the sample type with a unique identifier positioned on a sample container, and the sample preparation system includes an identifier capture device to identify the unique identifier, access the sample type protocol from the sample analysis information system, and execute the sample type protocol responsive to a queue associated with a sample order assigned to the sample type via the sample data manager.

17 Claims, 16 Drawing Sheets

(52) U.S. Cl.
CPC .................... *G01N 35/0095* (2013.01); *G01N 2035/00217* (2013.01); *G01N 2035/00831* (2013.01); *G01N 2035/00851* (2013.01); *G01N 2035/00881* (2013.01)

(56) References Cited

U.S. PATENT DOCUMENTS

| | | | | |
|---|---|---|---|---|
| 2005/0069978 | A1 | 3/2005 | Bower et al. | |
| 2005/0079099 | A1 | 4/2005 | Spain et al. | |
| 2006/0051239 | A1 | 3/2006 | Massaro | |
| 2006/0265133 | A1 | 11/2006 | Cocks et al. | |
| 2013/0065797 | A1* | 3/2013 | Silbert | G01N 35/00 506/39 |
| 2013/0295597 | A1 | 11/2013 | DeWitte et al. | |
| 2015/0212104 | A1 | 7/2015 | Furrer et al. | |
| 2017/0038402 | A1 | 2/2017 | Wiederin et al. | |
| 2017/0082585 | A1* | 3/2017 | Dewitte | G01N 30/7233 422/65 |
| 2019/0234974 | A1 | 8/2019 | Wiederin et al. | |

FOREIGN PATENT DOCUMENTS

| | | | |
|---|---|---|---|
| JP | 2012018126 | A | 1/2012 |
| JP | 2013155702 | A | 8/2013 |
| TW | 200911194 | A | 3/2009 |
| TW | I461690 | B | 11/2014 |
| TW | 201827831 | A | 8/2018 |
| WO | 03042788 | A2 | 5/2003 |
| WO | 2017143182 | A2 | 8/2017 |
| WO | 2018017771 | A1 | 1/2018 |

OTHER PUBLICATIONS

International Search Report for PCT/US2019/053516, dated Jan. 10, 2020.

Int'l Search Report and Written Opinion for PCT/US2019/053562 dated Jan. 13, 2020.

Office Action for Taiwan Application No. 108135602, dated Apr. 10, 2023.

Office Action for Taiwan Patent Application No. 10813560, dated May 4, 2023.

Office Action from Chinese Application No. 201980075972.8, dated Dec. 27, 2023.

Office Action from Chinese Application No. 201980076015.7, dated Dec. 27, 2023.

Office Action in Taiwan for Patent Application No. 108135601, dated Nov. 15, 2023.

Second Office Action in China for Patent Application No. 201980075972.8, dated Nov. 27, 2024.

Second Office Action in China for Patent Application No. 201980076015.7, dated Jan. 2, 2025.

Office Action in Taiwan for Patent Application No. 108135601, dated Jul. 10, 2024.

Third Office Action in China for Application No. 201980076015.7, dated May 31, 2025.

Third Office Action in China for Application No. 2019800759728, dated Apr. 21, 2025.

Fourth Office Action of Chinese Patent Application No. 201980075972.8, dated Jul. 3, 2025.

Decision of Rejection in China for Application No. 201980075972.8, dated Nov. 10, 2025.

Decision of Rejection from Taiwanese Application No. 108135602, dated Jun. 6, 2024.

Fourth Office Action for Chinese Application No. 201980076015.7, dated Aug. 18, 2025.

Office Action from Taiwanese Application No. 108135602, dated Sep. 16, 2025.

Third Office Action for Chinese Application No. 201980075972.8, dated Apr. 21, 2025.

* cited by examiner

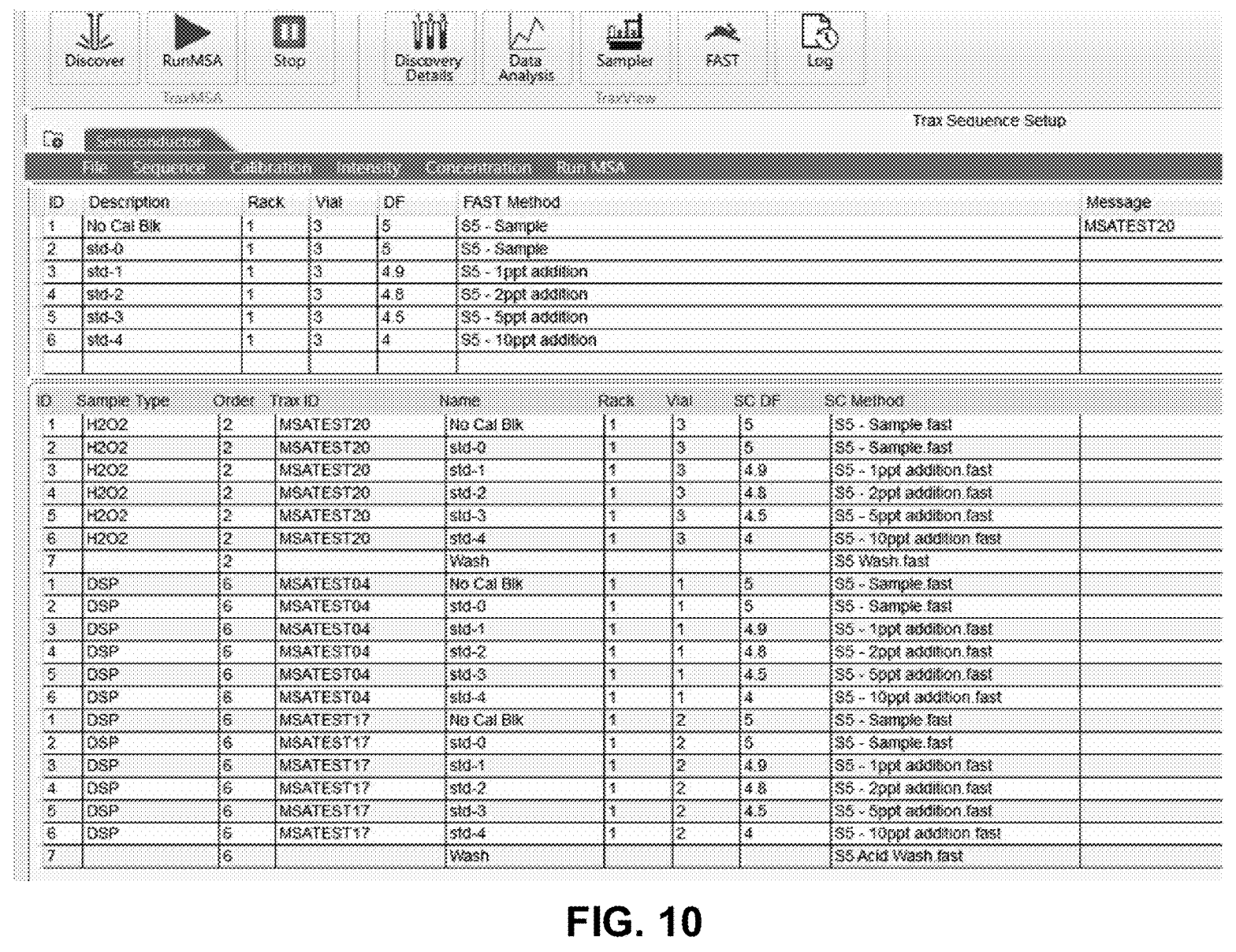

Discover RunMSA Stop Discovery Details Data Analysis Sampler FAST Log

Trax Sequence Setup

File Sequence Calibration Intensity Concentration Run MSA

| ID | Description | Rack | Vial | DF | FAST Method | Message |
|---|---|---|---|---|---|---|
| 1 | No Cal Blk | 1 | 3 | 5 | S5 - Sample | MSATEST20 |
| 2 | std-0 | 1 | 3 | 5 | S5 - Sample | |
| 3 | std-1 | 1 | 3 | 4.9 | S5 - 1ppt addition | |
| 4 | std-2 | 1 | 3 | 4.8 | S5 - 2ppt addition | |
| 5 | std-3 | 1 | 3 | 4.5 | S5 - 5ppt addition | |
| 6 | std-4 | 1 | 3 | 4 | S5 - 10ppt addition | |

| ID | Sample Type | Order | Trax ID | Name | Rack | Vial | SC DF | SC Method |
|---|---|---|---|---|---|---|---|---|
| 1 | H2O2 | 2 | MSATEST20 | No Cal Blk | 1 | 3 | 5 | S5 - Sample fast |
| 2 | H2O2 | 2 | MSATEST20 | std-0 | 1 | 3 | 5 | S5 - Sample.fast |
| 3 | H2O2 | 2 | MSATEST20 | std-1 | 1 | 3 | 4.9 | S5 - 1ppt addition.fast |
| 4 | H2O2 | 2 | MSATEST20 | std-2 | 1 | 3 | 4.8 | S5 - 2ppt addition.fast |
| 5 | H2O2 | 2 | MSATEST20 | std-3 | 1 | 3 | 4.5 | S5 - 5ppt addition.fast |
| 6 | H2O2 | 2 | MSATEST20 | std-4 | 1 | 3 | 4 | S5 - 10ppt addition.fast |
| 7 | | 2 | | Wash | | | | S5 Wash.fast |
| 1 | DSP | 6 | MSATEST04 | No Cal Blk | 1 | 1 | 5 | S5 - Sample.fast |
| 2 | DSP | 6 | MSATEST04 | std-0 | 1 | 1 | 5 | S5 - Sample.fast |
| 3 | DSP | 6 | MSATEST04 | std-1 | 1 | 1 | 4.9 | S5 - 1ppt addition.fast |
| 4 | DSP | 6 | MSATEST04 | std-2 | 1 | 1 | 4.8 | S5 - 2ppt addition.fast |
| 5 | DSP | 6 | MSATEST04 | std-3 | 1 | 1 | 4.5 | S5 - 5ppt addition.fast |
| 6 | DSP | 6 | MSATEST04 | std-4 | 1 | 1 | 4 | S5 - 10ppt addition.fast |
| 1 | DSP | 6 | MSATEST17 | No Cal Blk | 1 | 2 | 5 | S5 - Sample.fast |
| 2 | DSP | 6 | MSATEST17 | std-0 | 1 | 2 | 5 | S5 - Sample.fast |
| 3 | DSP | 6 | MSATEST17 | std-1 | 1 | 2 | 4.9 | S5 - 1ppt addition.fast |
| 4 | DSP | 6 | MSATEST17 | std-2 | 1 | 2 | 4.8 | S5 - 2ppt addition.fast |
| 5 | DSP | 6 | MSATEST17 | std-3 | 1 | 2 | 4.5 | S5 - 5ppt addition.fast |
| 6 | DSP | 6 | MSATEST17 | std-4 | 1 | 2 | 4 | S5 - 10ppt addition.fast |
| 7 | | 6 | | Wash | | | | S5 Acid Wash.fast |

FIG. 10

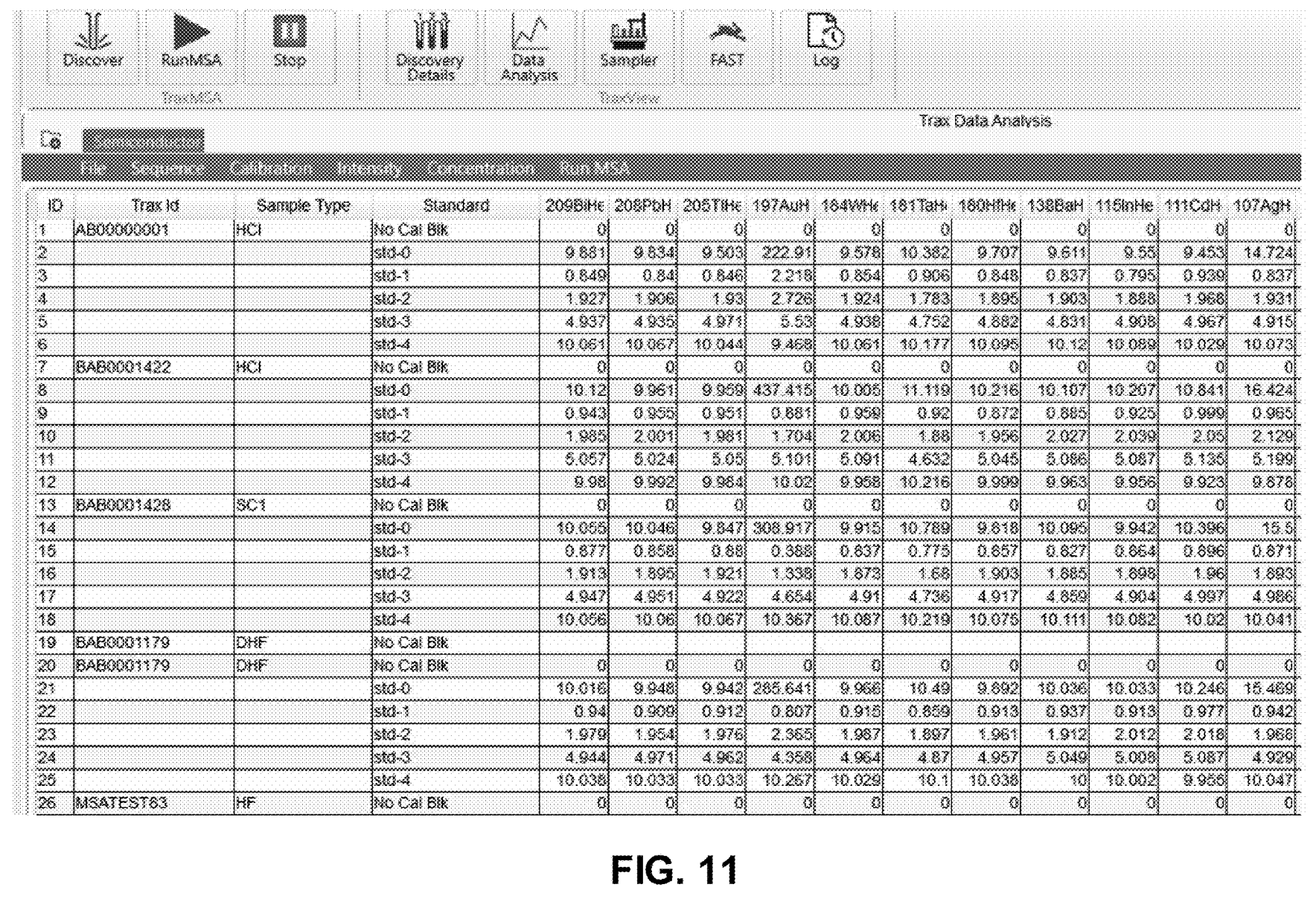

Discover RunMSA Stop Discovery Details Data Analysis Sampler FAST Log

Trax Data Analysis

| ID | Trax Id | Sample Type | Standard | 209BiHe | 208PbH | 205TlHe | 197AuH | 184WHe | 181TaHe | 180HfHe | 138BaH | 115InHe | 111CdH | 107AgH |
|---|---|---|---|---|---|---|---|---|---|---|---|---|---|---|
| 1 | AB00000001 | HCl | No Cal Blk | 0 | 0 | 0 | 0 | 0 | 0 | 0 | 0 | 0 | 0 | 0 |
| 2 | | | std-0 | 9.881 | 9.834 | 9.503 | 222.91 | 9.578 | 10.382 | 9.707 | 9.611 | 9.55 | 9.453 | 14.724 |
| 3 | | | std-1 | 0.849 | 0.84 | 0.846 | 2.218 | 0.854 | 0.906 | 0.848 | 0.837 | 0.795 | 0.939 | 0.837 |
| 4 | | | std-2 | 1.927 | 1.906 | 1.93 | 2.726 | 1.924 | 1.783 | 1.895 | 1.903 | 1.888 | 1.968 | 1.931 |
| 5 | | | std-3 | 4.937 | 4.935 | 4.971 | 5.53 | 4.938 | 4.752 | 4.882 | 4.831 | 4.908 | 4.967 | 4.915 |
| 6 | | | std-4 | 10.061 | 10.067 | 10.044 | 9.468 | 10.061 | 10.177 | 10.095 | 10.12 | 10.089 | 10.029 | 10.073 |
| 7 | BAB0001422 | HCl | No Cal Blk | 0 | 0 | 0 | 0 | 0 | 0 | 0 | 0 | 0 | 0 | 0 |
| 8 | | | std-0 | 10.12 | 9.961 | 9.959 | 437.415 | 10.005 | 11.119 | 10.216 | 10.107 | 10.207 | 10.841 | 16.424 |
| 9 | | | std-1 | 0.943 | 0.955 | 0.951 | 0.881 | 0.959 | 0.92 | 0.872 | 0.885 | 0.925 | 0.999 | 0.965 |
| 10 | | | std-2 | 1.985 | 2.001 | 1.981 | 1.704 | 2.006 | 1.88 | 1.956 | 2.027 | 2.039 | 2.05 | 2.129 |
| 11 | | | std-3 | 5.057 | 5.024 | 5.05 | 5.101 | 5.091 | 4.632 | 5.045 | 5.086 | 5.087 | 5.136 | 5.199 |
| 12 | | | std-4 | 9.98 | 9.992 | 9.964 | 10.02 | 9.958 | 10.216 | 9.999 | 9.963 | 9.956 | 9.923 | 9.878 |
| 13 | BAB0001428 | SC1 | No Cal Blk | 0 | 0 | 0 | 0 | 0 | 0 | 0 | 0 | 0 | 0 | 0 |
| 14 | | | std-0 | 10.055 | 10.046 | 9.847 | 308.917 | 9.915 | 10.789 | 9.818 | 10.095 | 9.942 | 10.396 | 15.5 |
| 15 | | | std-1 | 0.877 | 0.858 | 0.88 | 0.388 | 0.837 | 0.775 | 0.857 | 0.827 | 0.864 | 0.896 | 0.871 |
| 16 | | | std-2 | 1.913 | 1.895 | 1.921 | 1.338 | 1.873 | 1.68 | 1.903 | 1.885 | 1.898 | 1.96 | 1.893 |
| 17 | | | std-3 | 4.947 | 4.951 | 4.922 | 4.654 | 4.91 | 4.736 | 4.917 | 4.859 | 4.904 | 4.997 | 4.986 |
| 18 | | | std-4 | 10.056 | 10.06 | 10.067 | 10.367 | 10.087 | 10.219 | 10.075 | 10.111 | 10.082 | 10.02 | 10.041 |
| 19 | BAB0001179 | DHF | No Cal Blk | | | | | | | | | | | |
| 20 | BAB0001179 | DHF | No Cal Blk | 0 | 0 | 0 | 0 | 0 | 0 | 0 | 0 | 0 | 0 | 0 |
| 21 | | | std-0 | 10.016 | 9.948 | 9.942 | 285.641 | 9.966 | 10.49 | 9.692 | 10.036 | 10.033 | 10.246 | 15.469 |
| 22 | | | std-1 | 0.94 | 0.909 | 0.912 | 0.807 | 0.915 | 0.859 | 0.913 | 0.937 | 0.913 | 0.977 | 0.942 |
| 23 | | | std-2 | 1.979 | 1.954 | 1.976 | 2.365 | 1.987 | 1.897 | 1.961 | 1.912 | 2.012 | 2.018 | 1.966 |
| 24 | | | std-3 | 4.944 | 4.971 | 4.962 | 4.358 | 4.964 | 4.87 | 4.957 | 5.049 | 5.008 | 5.087 | 4.929 |
| 25 | | | std-4 | 10.038 | 10.033 | 10.033 | 10.267 | 10.029 | 10.1 | 10.038 | 10 | 10.002 | 9.956 | 10.047 |
| 26 | MSATEST63 | HF | No Cal Blk | 0 | 0 | 0 | 0 | 0 | 0 | 0 | 0 | 0 | 0 | 0 |

FIG. 11

AUTOMATIC SAMPLE AND STANDARD PREPARATION BASED ON RECOGNITION OF SAMPLE IDENTITY AND SAMPLE TYPE

CROSS-REFERENCE TO RELATED APPLICATIONS

The present application claims the benefit under 35 U.S.C. § 119(e) of U.S. Provisional Application Ser. No. 62/738,527, filed Sep. 28, 2018, and titled "AUTOSAMPLER WITH AUTOMATIC SAMPLE AND STANDARD PREPARATION BASED ON RECOGNITION OF SAMPLE IDENTITY" U.S. Provisional Application Ser. No. 62/738,527 is herein incorporated by reference in its entirety.

BACKGROUND

In many laboratory settings, it is often necessary to analyze a large number of chemical or biochemical samples at one time. In order to stream-line such processes, the manipulation of samples has been mechanized. Such mechanized sampling is commonly referred to as autosampling and is performed using an automated sampling device or autosampler.

SUMMARY

Systems and methods for managing a sample preparation and analysis system based on detected unique sample identities and locations are described having integrated informational systems to automatically identify unique samples and apply a specified analytical protocol based on the unique sample identity to queue and prepare samples and standards for analysis. A system embodiment includes, but is not limited to, a sample analysis information system communicatively connected with each of a sample data manager, a sample logging manager, and a sample preparation system, wherein the sample data manager stores on the sample analysis information system a sample type with a sample type protocol for execution by the sample preparation system, the sample logging manager assigns the sample type stored on the sample analysis information system with a unique identifier positioned on a sample container, and the sample preparation system includes an identifier capture device to identify the unique identifier, access the sample type protocol from the sample analysis information system, and execute the sample type protocol responsive to a queue associated with a sample order assigned to the sample type via the sample data manager.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

FIGURES

The Detailed Description is described with reference to the accompanying figures. The use of the same reference numbers in different instances in the description and the figures may indicate similar or identical items.

FIG. 10 is an illustration of an example user interface of the sample analysis information system showing a sample queue assigned according to sample types identified by the sample preparation system in accordance with example implementations of the present disclosure.

FIG. 11 is an illustration of an example user interface of the sample analysis information system showing example concentration data of various elements in accordance with example implementations of the present disclosure.

DETAILED DESCRIPTION

Overview

Figure 1:
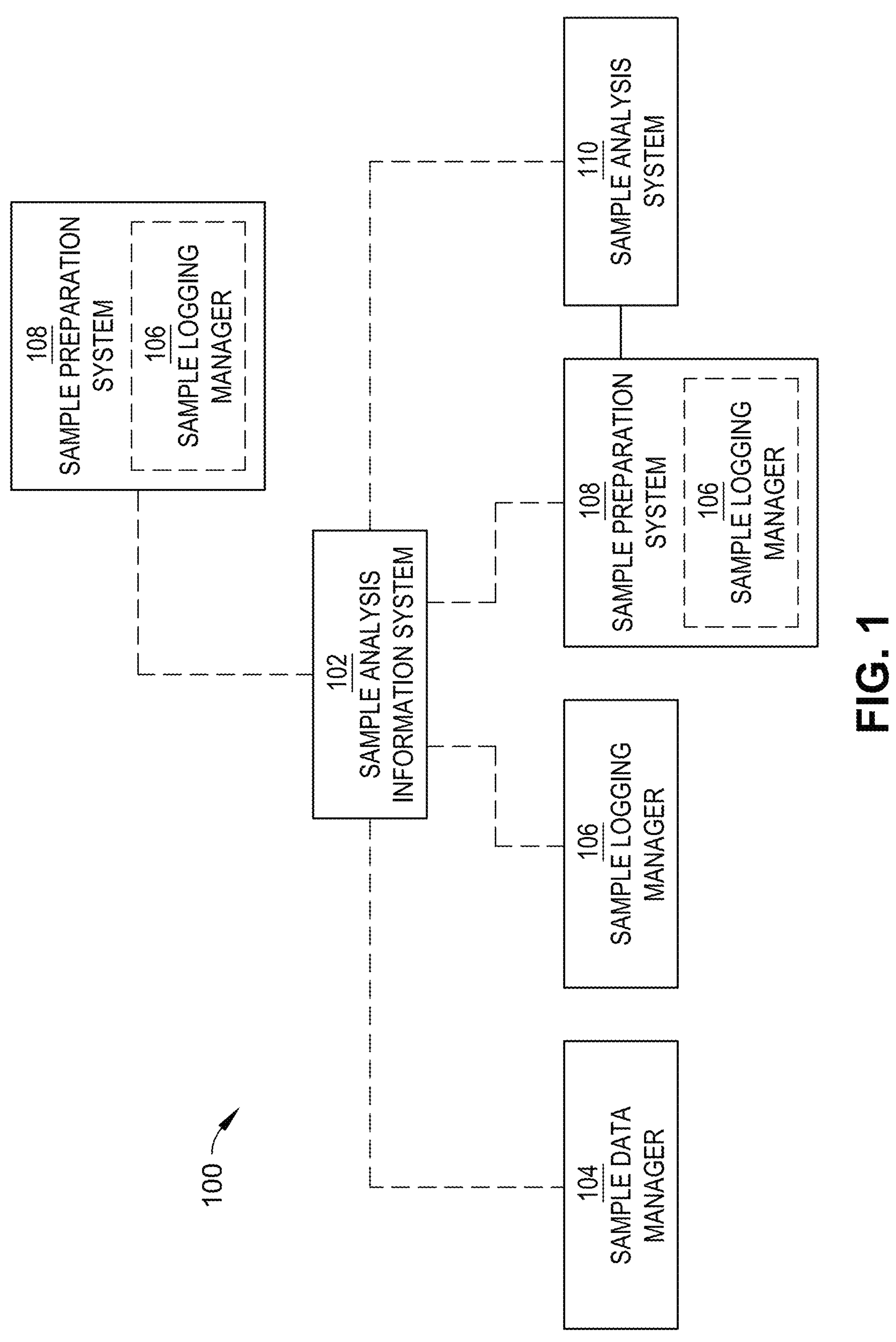
FIG. 1 is a diagram of a sample preparation system network for automatically identifying unique samples and applying a specified sample preparation protocol based on the unique sample identity to queue and prepare samples and standards for analysis in accordance with example implementations of the present disclosure.
Figure 2:
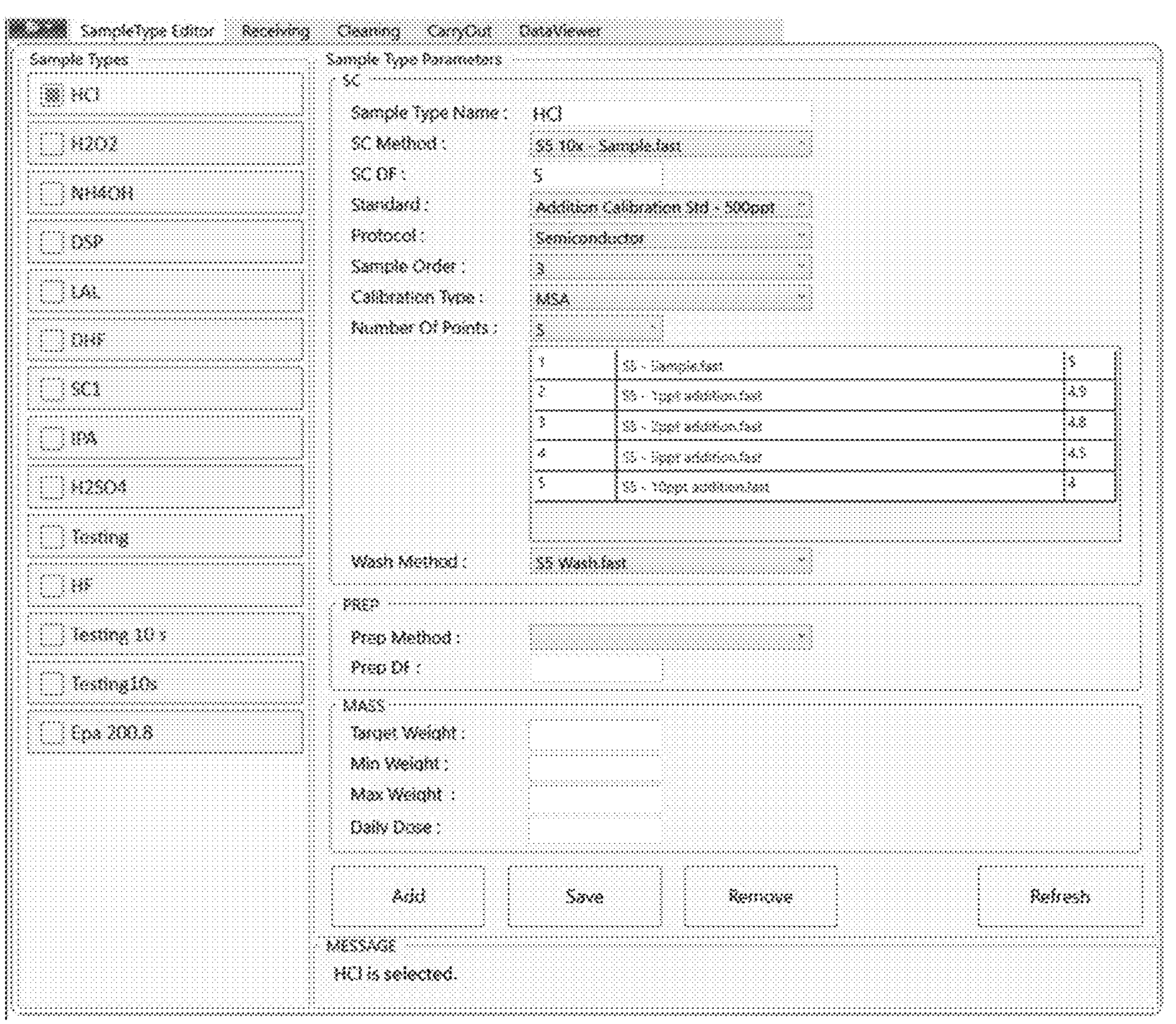
FIG. 2 is an illustration of an example user interface of a sample data manager in accordance with example implementations of the present disclosure.

Often in laboratory or industry settings, large numbers of samples are analyzed. Autosamplers are frequently used to gather and introduce samples for subsequent testing of the composition of these samples. Using an autosampler typically allows more samples and other solutions to be prepared and tested as compared to manual preparation methods. During the sample preparation process, multiple containers may be used to prepare samples, prepare standards (e.g., to generate one or more calibration curves), introduce standard spikes to a sample, hold various reagents, hold samples, or the like. Determination of trace elemental concentrations or amounts in a sample can provide an indication of purity of the sample, or an acceptability of the sample for use as a reagent, reactive component, or the like. For instance, in certain production or manufacturing processes (e.g., mining, metallurgy, semiconductor fabrication, pharmaceutical processing, etc.), the tolerances for impurities can be very strict, for example, on the order of fractions of parts per billion. For example, semiconductor processes can require ultralow detection limits for impurities in process chemicals including, but not limited to, ultrapure water (UPW) for washing wafers, isopropyl alcohol (IPA) for drying wafers, hydrogen peroxide ($H_2O_2$), ammonia solution ($NH_4OH$), and the like. Failure to detect ultralow concentrations of impurities in such process chemicals can ruin a semiconductor wafer, such as by precipitating such impurities out of solution and onto the wafer (e.g., depositing a metallic impurity or other conductivity hazard onto the wafer, such as through precipitation of the impurity out of solution, the wafer acting as a concentrator surface for the impurity, or the like).

The ordering of the various containers available to an autosampler can affect the accuracy of data generated from analysis of the samples contained therein. For instance, autosampling systems can rely on a specific or predetermined arrangement of sample containers held within a sample rack while the probe is introduced to each sample container in a serial manner. Results of the analysis of the samples are then tied to the specific or predetermined arrangement following the serial progression. As such, the results of such analysis can be erroneous if an individual deviates from the specific or predetermined arrangement when placing sample containers in the sample rack(s). The risk of error can increase if the individual at the autosampler differs from the individual handling the initial gathering of the sample. For instance, mislabeling or misidentifying a sample during or after transit from a sampling point can cause information associated with the sample to be erroneously associated with another sample, such as through misplacement of the sample container within the sample rack, misplacement of a sample within a particular sample container, or the like.

Further, an individual can implement an incorrect sample preparation protocol or sample analysis protocol for a particular sample, even when the sample is appropriately identified. For instance, the individual can utilize an incorrect calibration protocol, an incorrect dilution factor, introduce an incorrect fluid to the sample, fail to separate a sample into a sufficient number of sample replicates, or the like for a sample, thereby affecting the usefulness of the results of analysis of the sample. This risk increases as the number of individuals performing the sample preparation increases, which can be problematic for laboratories or industries as training and oversight costs increase. Still further, the particular ordering of samples handled by a sample preparation system can contribute to the performance of a system. For example, incomplete washout of sample between different sample types can lead to a chemical reaction within fluid lines of the system, leading to skewed analytical results or even instrument damage (e.g., testing a base immediately prior to testing a strong acid).

Accordingly, a system for managing a sample preparation and analysis system is described having integrated informational systems to automatically identify unique samples and apply a specified analytical protocol based on the unique sample identity to queue and prepare samples and standards for analysis. A system embodiment includes a sample analysis information system in communication with each of a sample data manager, a sample logging manager, a sample preparation system, and a sample analysis system.

In example implementations, the sample data manager provides an individual with a user interface to set sample handling protocols for different sample types (or groups, classes, etc.) that are desired for analysis by an analytic device, such as inductively coupled plasma spectrometry instrumentation (e.g., an ICP mass spectrometer (ICPMS), an ICP atomic emission spectrometer (ICPAES), etc.). For example, a first sample type can include a first acid (e.g., sulfuric acid—$H_2SO_4$), a second sample type can include a peroxide (e.g., hydrogen peroxide—$H_2O_2$), a third sample type can include a second acid (e.g., nitric acid—$HNO_3$), and so forth, each with the ability to have differing sample handling protocols unique to the sample type. When a sample is presented for analysis, the specific sample handling protocol set via the sample data manager is automatically executed by the sample preparation system which can initiate the sample handling protocols through communication with the sample analysis information system upon identification of a sample identity of the sample presented for analysis or upon selection of the sample type to be associated with the sample in a particular sample container.

The sample identity is assigned to a sample in a sample container through user interface with the sample logging manager. For example, with the sample logging manager, a user scans an identifier (e.g., a bar code, a 2-D bar code, etc.) positioned on a sample container and inputs information in the sample logging manager associated with the sample container including, but not limited to, an identity of the user interacting with the sample logging manager (e.g., via a unique login), a date of sample data entry, a time of sample data entry, a source of the sample (e.g., sampling point within a facility, a customer source, etc.), comments associated with the sample, or the like. The labeled sample containers can be placed in a sample rack or on a sampling deck of the sample preparation system without a specific arrangement of the containers with respect to each other. In implementations, the sample preparation system dynamically scans for the presence of the labeled sample containers during a discovery operation and arranges sample preparation of the samples within the containers based on compiling the information associated with the samples entered via the sample logging manager and the sample type protocols entered via the sample data manager through communication with the sample analysis information system. The sample preparation system queues and processes samples according to the identified sample types, where the locations of the sample within the sample racks dictates the positioning of the sample probe during the queuing rather than a static serial progression through the rack positions.

Example Implementations

Referring to FIGS. 1 through 13 a system 100 for managing a sample preparation and analysis system is shown in accordance with example implementations of the present disclosure. The system 100 generally includes a sample preparation system network for automatically identifying unique samples and applying a specified analytical protocol based on the unique sample identity to prepare samples and standards for analysis and to queue the handling of the samples. With reference to FIG. 1, the system 100 is shown including a sample analysis information system 102 communicatively connected with each of a sample data manager 104, a sample logging manager 106, a sample preparation system 108, and a sample analysis system 110. In general, the sample data manager 104 provides a platform to view data and edit protocols associated with sample preparation and analysis of samples handled by the system 100 via communication with the sample analysis information system 102, the sample logging manager 106 provides a platform to associate a fluid sample with a specific sample container based on a unique sample identifier positioned on a sample container and to assign a sample type to the sample in the specific sample container, the sample preparation system 108 provides a platform to execute a sample protocol associated with the given sample type (e.g., to dilute the sample, divide a sample into multiple containers, add fluids or reagents to the sample, provide a specified weight boundary to prepare a sample by weight, prepare a number of calibration analyses, and the like), and the sample analysis system 110 receives a sample from one or more sample preparation systems 108 for analytic determination of one or more components present in the sample. The sample analysis system 110 is coupled to the sample preparation system 108 to receive a fluid sample for analytic determination of one or more elements contained therein and can include, but is not limited to, inductively coupled plasma spectrometry instrumentation, such as an ICP mass spectrometer (ICPMS), an ICP atomic emission spectrometer (ICPAES), etc.

In implementations, the sample preparation system 108 includes a sample logging manager 106 to associate a sample type with a sample container at the sample preparation system 108 (e.g., by scanning a sample identifier positioned on a sample container and/or on a sample holder). The sample preparation system 108 can include, for example, one or more of a mass balance (e.g., described with reference to FIG. 6), a sample probe to remove fluids from a sample container and add fluids to a sample container (e.g., for offline sample preparation), an inline dilution system (e.g., for automated inline sample dilution and calibration standard preparation), and the like. In implementations, the sample preparation system 108 includes a sample probe in fluid communication with an inline sample dilution system to receive the sample from the sample probe and prepare the sample for analysis by the sample analysis system 110, such as by introducing a diluent, a standard, a spike fluid, or combinations thereof, inline to the sample according to one or more sample preparation protocols established by the sample data manager 104 and associated with a particular sample via the sample logging manager 106. For example, the sample preparation system 108 can include one or more of a variable inline dilution system described in U.S. patent application Ser. No. 13/656,972 incorporated herein by reference, an inline dilution and autocalibration system described in U.S. patent application Ser. No. 15/368,803 incorporated herein by reference, a system for inline sample dilution described in U.S. patent application Ser. No. 16/119,228 incorporated herein by reference, or components or combinations thereof.

In implementations, the sample analysis information system 102 includes a database (e.g., a structured query language (SQL) database) communicatively connected with each of the sample data manager 104, the sample logging manager 106, the sample preparation system 108, and the sample analysis system 110 via one or more networks. The sample analysis information system 102 can also be communicatively connected with a laboratory information management system (LIMS), one or more client devices (e.g., mobile computing device), and the like to receive or transmit data for managing sample preparation. The networks can include a variety of different communication pathways and network connections which may be employed, individually or in combinations, to communicate among the components of the system 100. Thus, the one or more networks may be representative of communication pathways achieved using a single network or multiple networks. Further, the one or more networks are representative of a variety of different types of networks and connections that are contemplated including, but not necessarily limited to: the Internet; an intranet; a Personal Area Network (PAN); a Local Area Network (LAN) (e.g., Ethernet); a Wide Area Network (WAN); a satellite network; a cellular network; a mobile data network; wired and/or wireless connections; and so forth. Examples of wireless networks include, but are not necessarily limited to: networks configured for communications according to: one or more standard of the Institute of Electrical and Electronics Engineers (IEEE), such as 802.11 or 802.16 (Wi-Max) standards; Wi-Fi standards promulgated by the Wi-Fi Alliance; Bluetooth standards promulgated by the Bluetooth Special Interest Group; and so on. Wired communications are also contemplated such as through Universal Serial Bus (USB), Ethernet, serial connections, and so forth.

The sample analysis information system 102 hosts or otherwise stores information associated with sample type analysis protocols, sample name, sample type, dilution method, dilution factor, standard type, sample handling protocol, calibration type, sample order, number of calibration points, wash method, logistic information associated with a given sample, and the like. Such sample information can be entered, modified, or removed through interaction of an individual with a user interface associated with one or more of the sample data manager 104, the sample logging manager 106, and the sample preparation system 108, or automatically from the sample data manager 104, the sample logging manager 106, or the sample preparation system 108, for example, to implement the appropriate sample preparation or analysis protocols for a specific sample or samples. Access to each of the sample analysis information system 102, the sample data manager 104, the sample logging manager 106, and the sample preparation system 108 can be restricted based on user security or access credentials. For example, a user, such as a laboratory technician tasked with gathering a sample may have a login credential with security access to the sample logging manager 106 and the sample preparation system 108, but with insufficient security credentials to access the sample data manager 104. Another individual, such as a laboratory manager tasked with overseeing the consistency of laboratory sampling and processing may have a login credential with security access to each the sample data manager 104, the sample logging manager 106, and the sample preparation system 108.

Sample Data Manager

The sample data manager 104 provides an interface for an individual to view data and edit protocols associated with sample preparation and analysis of samples handled by the system 100. An example user interface of the sample data manager 104 is shown with reference to FIG. 2. The sample data manager 104 permits a user (e.g., a lab manager) to introduce specific sample type protocols into the system 100, such that assignment of a sample type to a sample container or identification of a sample of the specific sample type at the sample preparation system 108 will cause the sample preparation system 108 to automatically execute the sample type protocol for that sample. In implementations, the system 100 requires that a user have modification authority to add or modify specific sample type protocols via the sample data manager 104, which can ensure that consistent protocols are utilized by the system 100 to prepare samples for analysis by the sample analysis system 110. A sample type protocol can include, but is not limited to, a specified sample preparation method, a standard type, an analysis protocol, a sample order, a calibration type, a number of calibration points, a dilution factor associated with each calibration point, a wash method, preparation method, target sample weights or volumes, and the like.

The sample type protocol or portions thereof to be executed by the sample preparation system 108 can depend on the hardware of the sample preparation system 108 at which a sample container is located. For example, when the sample preparation system 108 includes a mass balance (e.g., shown in FIG. 7A), the sample preparation system 108 can execute portions of the sample type protocol associated with target sample weights. As another example, when the sample preparation system 108 includes an autosampler with a sample probe to move fluids between containers (e.g., shown in FIGS. 7B and 7C), the example preparation system 108 can execute portions of the sample type protocol associated with offline sample preparation including, but not limited to, moving sample into multiple sample containers for replicates, adding fluids to a sample (e.g., acid addition for sample digestion), diluting sample, and the like. As a further example, when the sample preparation system 108 is fluidically coupled to the sample analysis system 110, the example preparation system 108 can execute portions of the sample type protocol associated with preparation of standard solutions to build calibration curves, inline standard spikes, inline dilution, and the like. The specified sample preparation method can include factors associated with a script used by the sample preparation system 108 to coordinate operations of pumps and valves to facilitate the desired transfer, dilution, standard introduction, and handling of a fluid sample for analysis by the sample analysis system 110. The specified sample preparation method can include a sample size that is associated with a sample loop or sample holding line of the sample preparation system 108. The analysis protocol can include, but is not limited to, a list of which analytes that should be analyzed by the sample analysis system 110, calibration levels for each standard calibration (e.g., standard 1 for a selected element is 1 ppt, standard 2 for the selected element is 2 ppt, standard 3 for the selected element is 5 ppt, standard 4 for the selected element is 10 ppt, etc.), dilution factors for each standard calibration, and the like. In implementations, only the data associated with the analytes identified in the analysis protocol is populated in the sample analysis information system 102 from results determined by the sample analysis system 110, even if the sample analysis system 110 generates data for elements not in the analysis protocol for a given sample type. The sample analysis information system 102 can store information associated with data for elements not in the analysis protocol for later review or review by a subset of users of the system 100 (e.g., those with modification authority within the system 100).

The sample order of the sample type protocol provides a relative order of handling a given sample type by the sample preparation system 108 as compared to another sample type. For example, a sample type of hydrochloric acid can have a sample order assigned in the sample data manager 104 of 3, whereas a sample type of hydrogen peroxide can have a sample order assigned in the sample data manager 104 of 2, and a sample type of hydrogen fluoride can have a sample order assigned in the sample data manager 104 of 1. Thus, if the sample preparation system 108 has samples having a sample type assigned via the sample logging manager 106 as hydrogen peroxide and samples having a sample type assigned via the sample logging manager 106 as hydrochloric acid for processing, the sample preparation system 108 will handle the hydrogen peroxide samples prior to handling the hydrochloric acid samples due to the lower sample order assigned to the hydrogen peroxide samples. The sample order provides a user-defined ordering of samples with respect to other samples to enhance performance of the system 100, such as by avoiding or mitigating chemical reactions within system fluid lines if incomplete washout of sample occurs. Generation of a sample queue based on sample type to be handled by the sample preparation system 108 is discussed further herein with respect to FIGS. 9A and 9B.

The calibration type of the sample type protocol designates how often a calibration curve is built, whether an offline standard dilution (e.g., using the sample probe to dispense a standard and diluent together within a container) or an inline standard dilution or addition (e.g., an MSA standard) is performed by the sample preparation system 108, and the like. In implementations the calibration type is one of an external calibration type, an MSA calibration type, or an addition calibration type. The external calibration type directs the sample preparation system 108 to prepare a single calibration curve followed by analysis of all samples queued for analysis. The MSA calibration type directs the sample preparation system 108 to prepare a separate calibration curve for each individual sample queued for analysis. The addition calibration type directs the sample preparation system 108 to prepare a separate calibration curve for each sample type of samples queued for analysis (i.e., a first calibration curve for all samples having a first sample type, a second calibration curve for all samples having a second sample type, etc.). The number of calibration points of the sample type protocol designates how many standard points are measured to build the standard calibration curve, where dilution factors for each point can be set. For instance, a first calibration point is obtained through analysis by the sample analysis system 110 of a standard at a first dilution factor, a second calibration point is obtained through analysis by the sample analysis system 110 of the standard at a second dilution factor, and so on for each calibration point associated with the sample type protocol.

The wash method of the sample type protocol designates a script used by the sample preparation system 108 to coordinate operations of pumps and valves to facilitate the desired wash protocol (e.g., volume of rinse fluid, time of rinse, number of rinses, type of rinse fluid(s), etc.), where different sample types can have different wash methods. The preparation method provides customizable protocols for sample preparation, such as offline autodilution or addition of fluids to a sample, preparation of sample replicates by moving fluid from a first sample container to one or more additional sample containers, and the like. For instance, the sample preparation system 108 can execute the preparation method of the sample type protocol to control a sample probe of the sample preparation system 108 or a separate autosampler to dispense a sample/standard and diluent or other fluid together within a container. Alternatively or additionally, the preparation method can include inline dilution or fluid addition. Target sample weights or volumes refers to syringe control of the sample probe 114 to take a particular volume of sample, such as a solid sample suspended in solution or a sample having a particular density to draw consistent amounts for analysis between samples. For sample protocols involving sample weights, the target sample weight can provide a specified weight boundary (e.g., a minimum target weight and a maximum target weight) for a particular sample type.

Sample Logging Manager

Figure 3:
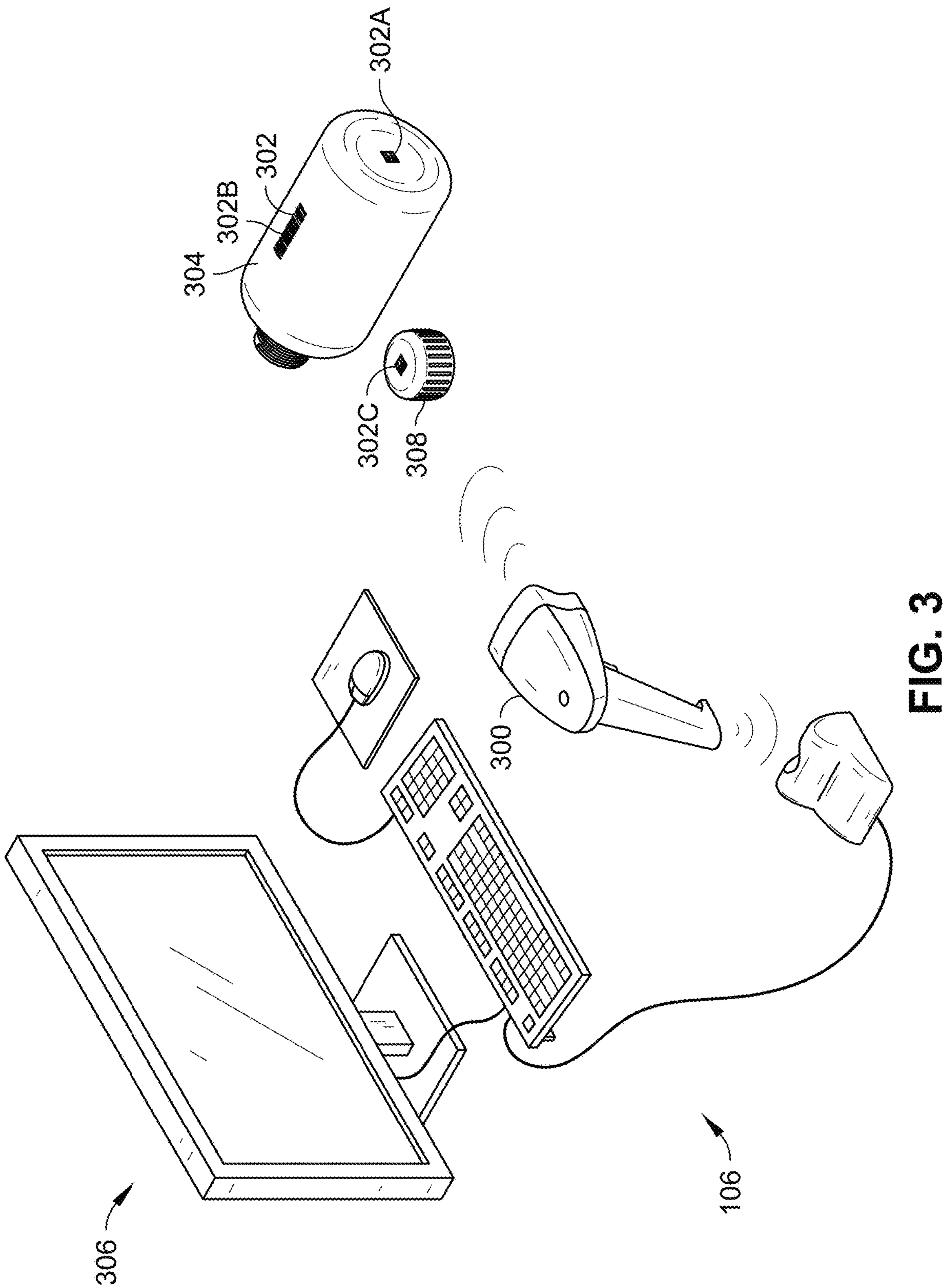
FIG. 3 is a view of a scanner of a sample logging manager to record information associated with a unique identity of a sample container with the sample analysis information system in accordance with example implementations of the present disclosure.
Figure 4:
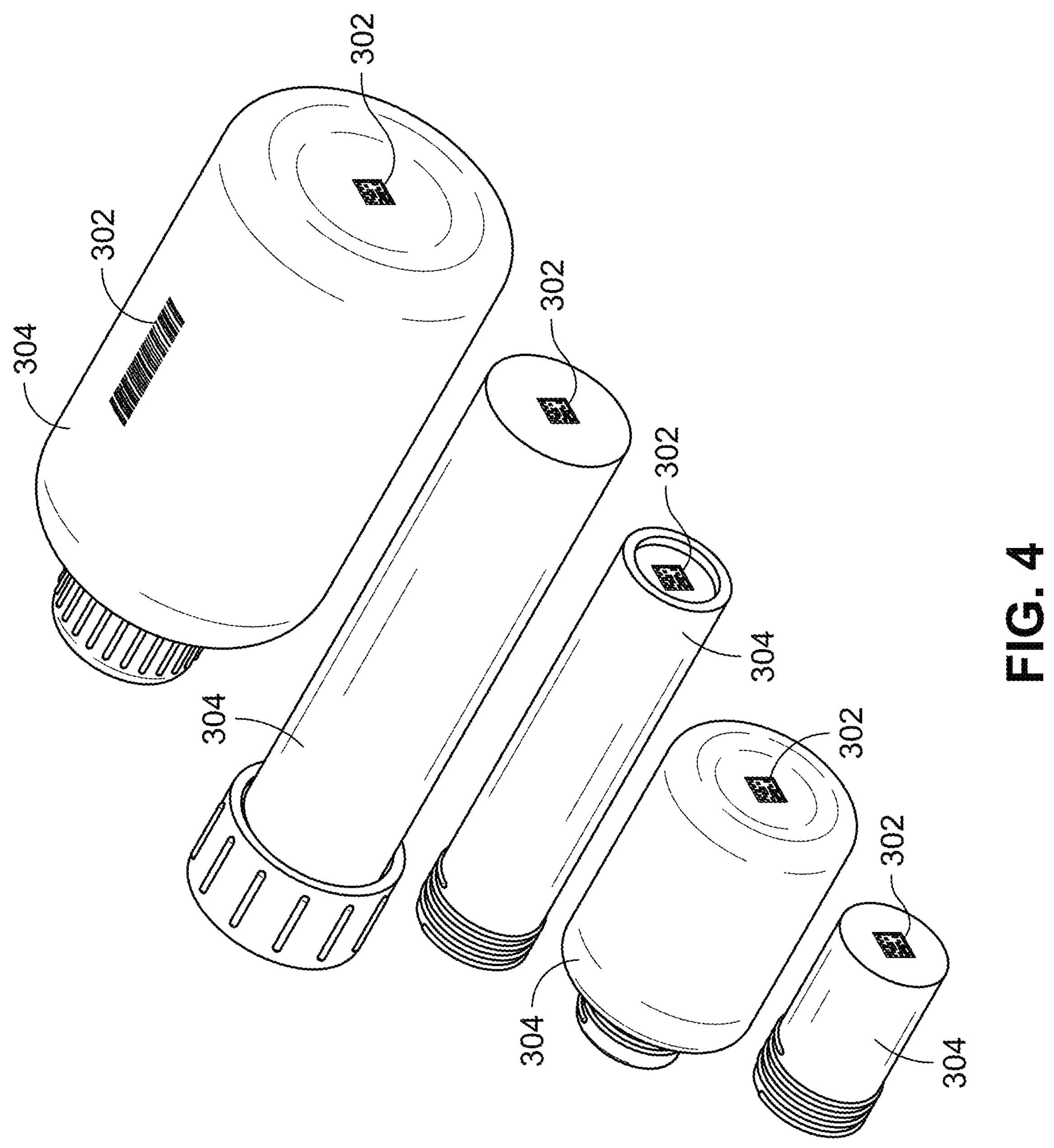
FIG. 4 is an isometric view of example sample containers having unique identifiers to be scanned by the sample logging manager and sample preparation system.
Figure 5:
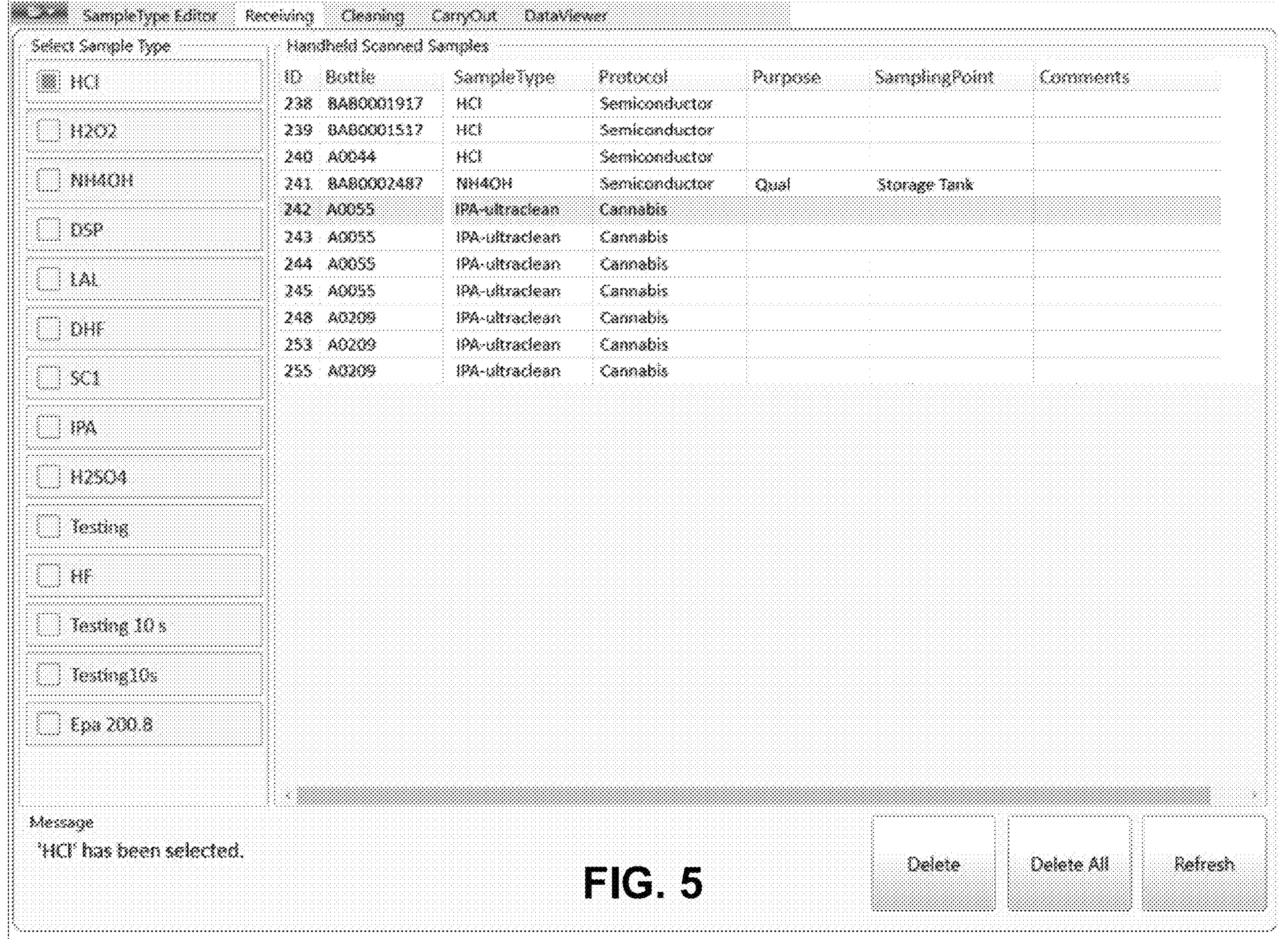
FIG. 5 is an illustration of an example user interface of a sample logging manager in accordance with example implementations of the present disclosure.

The sample logging manager 106 provides an interface for an individual (e.g., a lab technician) to associate a fluid sample with a specific sample container based on a unique sample identifier positioned on a sample container. Referring to FIG. 3, the sample logging manager 106 can include a bar code scanner 300, optical device, or other recognition device to scan a sample identifier 302 positioned on a sample container 304. For example, a user can enter via a computing device 306 information associated with the sample to have the information associated with the sample identifier 302 via the sample logging manager 106 to be stored at the sample analysis information system 102. Alternatively or additionally, the sample logging manager 106 is included in one or more sample preparation systems 108 to permit an individual to select a particular sample type to be associated with a specific sample container (e.g., via the sample identifier 302). For example, the sample preparation system 108 can include a scanner integrated in a mass balance to scan the unique identifier 302 on the sample container 304 placed on the mass balance, where the mass balance communicates with the sample analysis information system 102 to identify the sample type previously assigned to the sample container 304 or to assign a sample type to the sample container 304 is no sample type was previously assigned. As another example, the sample preparation system 108 can include a scanner (e.g., identifier capture device 708 described herein) to facilitate logging of sample information via the sample logging manager 106 when sample containers 304 are positioned on a deck of an autosampler table for offline sample preparation or inline sample preparation for analysis.

In implementations, the sample identifier 302 is unique to the specific sample container 304, such that different sample containers 304 have different sample identifiers 302. The sample identifier 302 can include a one dimensional barcode or a data matrix two-dimensional (2D) barcode, such as a 12×12 matrix, a 13×13 matrix, a 14×14 matrix, or any other suitable matrix. While square matrices are provided as example data matrix barcodes, it is contemplated that rectangular matrices also may be utilized. The sample identifier 302 can include other identification indicia including, but not limited to: characters and/or patterns configured for recognition by an optical camera or sensor; radio frequency identification (RFID) tags; raised surfaces for recognition by touch sensors, optical sensors, and the like; illumination sources configured to generate a particular color (or wavelength), pattern of light, etc.; other identification indicia configured for recognition by an identifier capture device of the sample preparation system 108; and so forth. Example sample containers 304 are provided in FIGS. 3 and 4.

A sample container 304 can include a plurality of sample identifiers 302, which can be of the same or different type with respect to each other. For example, referring to FIG. 3, the sample container 304 is shown with a first container identifier 302A and a second container identifier 302B, with a cap 308 having a third container identifier 302C. The first container identifier 302A is shown as a data matrix two-dimensional barcode, whereas the second container identifier 302B is shown as a one-dimensional barcode. Each of the first container identifier 302A and the second container identifier 302B can uniquely identify the sample container 304 and can permit multiple scanning devices to identify the sample container 304. For example, the first container identifier 302A can be accessible to and identified by the identifier capture device of the sample preparation device 208 described herein, and the second container identifier 302B can be accessible to and identified by the bar code scanner 300 or other scanner available in a lab or in the field. The third container identifier 302C on the cap 308 can uniquely identify the cap 308 with respect to any other cap or with respect to any container or container body. As such, data associated with the cap 308 (e.g., a contaminate level or contaminate history) can be tracked via the third container identifier 302C independently of data associated with the sample container 304 or sample held or previously held within the sample container 304 on which the cap 308 is located or previously located.

A user can input information associated with a sample via the sample logging manager 106 (e.g., via computing device 306, via a computing device communicatively connected with a sample preparation system 108, a mobile computing device, or other terminal) following scanning of the sample identifier 302, where such data is stored at the sample analysis information system 102 for later retrieval to facilitate execution of sample type protocols and sample queuing at the sample preparation device 108. An example user interface of the sample logging manager 106 is shown with reference to FIG. 5. In implementations, the user can select a sample type from a list of pre-entered sample types entered into the system 100 via the sample data manager 104, where the sample type is then associated with the unique sample identifier 302 throughout the system 100 through communication coupling between the components of the system 100 with the sample analysis information system 102. The sample logging manager 106 can also facilitate entering of additional information to be associated with the unique identifier 302 including, but not limited to, an identity of the user interacting with the sample logging manager 106 (e.g., via a unique login), a date of sample data entry, a time of sample data entry, a source of the sample (e.g., sampling point within a facility, a customer source, etc.), comments associated with the sample, or the like.

The sample logging manager 106 automatically associates a sample type protocol with the unique identifier 302 based on the sample type selected by the user to provide the appropriate protocols to the sample preparation system 108 without further interaction from the user interfacing with the sample logging manager 106. Since the sample data manager 104 manages the sample types and sample type protocols independently from the sample logging manager 106, the sample types and sample type protocols can be managed and monitored to provide consistent protocols to be used throughout a facility or group of facilities for chemical analysis. For example, a lab manager, technical manager, or group of individuals can establish common protocols for use throughout a facility or group of facilities, independent of the number of individuals who obtain the samples for analysis. As such, hundreds of samples and more can be processed by the system 100 with appropriate and consistent sample protocols for preparation of the samples by the sample preparation system 108 and analysis of the samples by the sample analysis system 110. Accordingly, the sample type protocols can be managed through the sample data manager 104 for consistency between samples having the same sample type, as opposed to relying on additional data entry related to sample type protocols (independent of selecting the sample type via the sample logging manager 106) during the gathering of samples or introducing the samples to an autosampling device.

Sample Preparation System

Samples located at the sample preparation system 108 can be scanned to determine whether a unique identifier 302 is located on the sample container 304 or whether a unique identifier 302 present on the sample container 304 is associated with a sample type (i.e., previously entered via the sample logging manager 106). If no unique identifier 302 is present or if no sample type is already associated with a unique identifier 302 that is present, the sample logging manager 106 can be utilized to assign a sample type to the sample container 304 at the sample preparation system 108. The sample preparation system 108 can include, for example, one or more of a mass balance, a sample probe to remove fluids from a sample container and add fluids to a sample container (e.g., for offline sample preparation), an inline dilution system (e.g., for automated inline sample dilution and calibration standard preparation), and the like.

Figure 6:
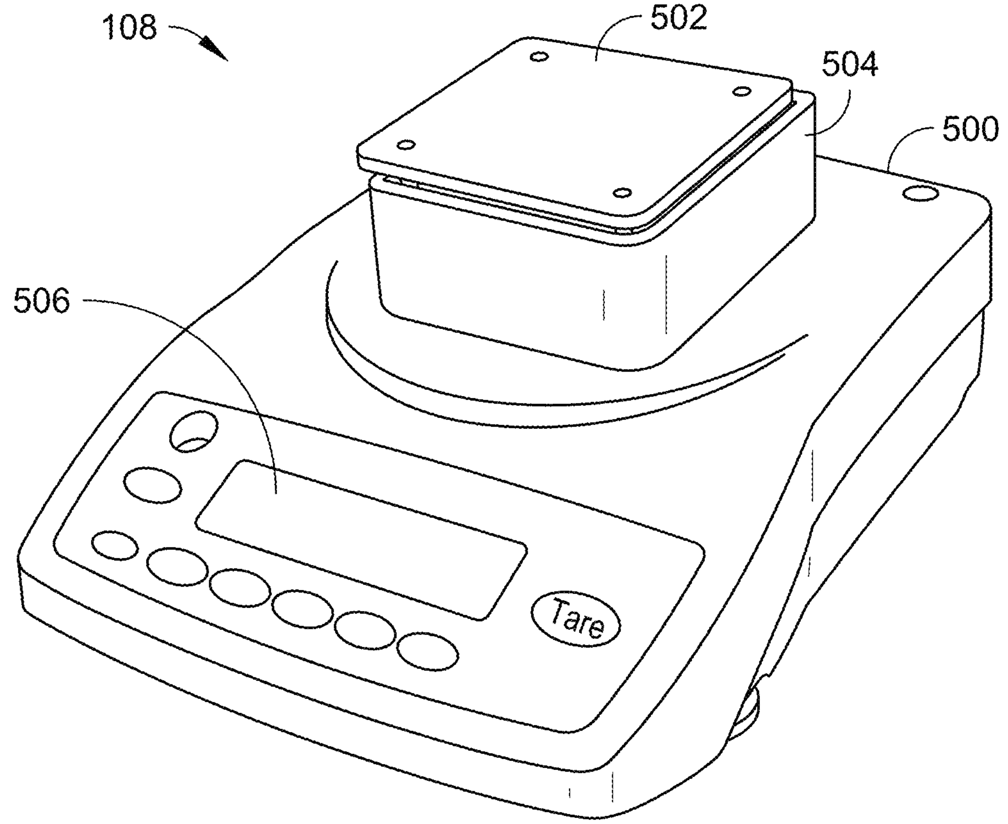
FIG. 6 is an isometric view of a sample preparation system having a mass balance to measure a weight of a sample and facilitate providing a specified weight boundary to prepare a sample by weight in accordance with example implementations of the present disclosure.

Referring to FIG. 6, the sample preparation system 108 is shown to include a mass balance 500 having a surface 502 to support a sample container 304 for weighing the sample container 304 and any sample present therein. The mass balance 500 includes a scanner to recognize the sample identifier 302 positioned on the sample containers 304 (e.g., on a bottom surface of the sample container 304). The scanner can include, for example, one or more of a barcode scanner, an RFID reader, a camera, an optical detector, or the like. For example, the mass balance 500 can include a housing 504 beneath the surface 502 to house the scanner oriented to scan through the surface 502 to detect sample identifiers 302 positioned on the surface 502. In implementations, the surface 502 includes a light transmissive material to permit detection of the sample identifiers 302 by the scanner through the surface 502. In implementations, the mass balance 500 is communicatively connected to the sample analysis information system 102 to determine whether a sample identifier 302 detected by the mass balance 500 is associated with a sample type. For instance, if a user previously associated a sample type with the unique sample identifier 302 in the sample container 304, the mass balance can access the appropriate sample type protocol established for the sample type via the sample data manager 104. The sample type protocol for the mass balance 500 can include a minimum target weight of sample and a maximum target weight of sample. For example, the sample container 304 can be placed on the surface 502, where a tare function of the mass balance 500 can zero the weight of the sample container 304. A display (e.g., display 506 on the mass balance 500, a display of a computing device communicatively coupled with the mass balance 500, or combinations thereof) can show the current weight of sample in the sample container 304 as sample is introduced to the sample container 304. The mass balance can compare the current weight of sample to the minimum target weight and maximum target weight assigned by the sample type associated with the unique identifier 302. In implementations, the display shows the current weight of sample held on the mass balance 500 in a first format when the current weight is below the minimum weight of sample or above the maximum weight of sample and shows the current weight of sample held on the mass balance 500 in a second format when the current weight is at the minimum weight of sample, between the minimum weight of sample and the maximum weight of sample, or at the maximum weight of sample, responsive to execution of the sample type protocol. For example, when the current weight is outside of the minimum weight or maximum weight, the display can show the current weight in a first color, size, or font (e.g., red color), and when the current weight is at the minimum weight, at the maximum weight, or between the minimum weight and maximum weight, the display can show the current weight in a second color, size, or font (e.g., green color).

Figure 7A:
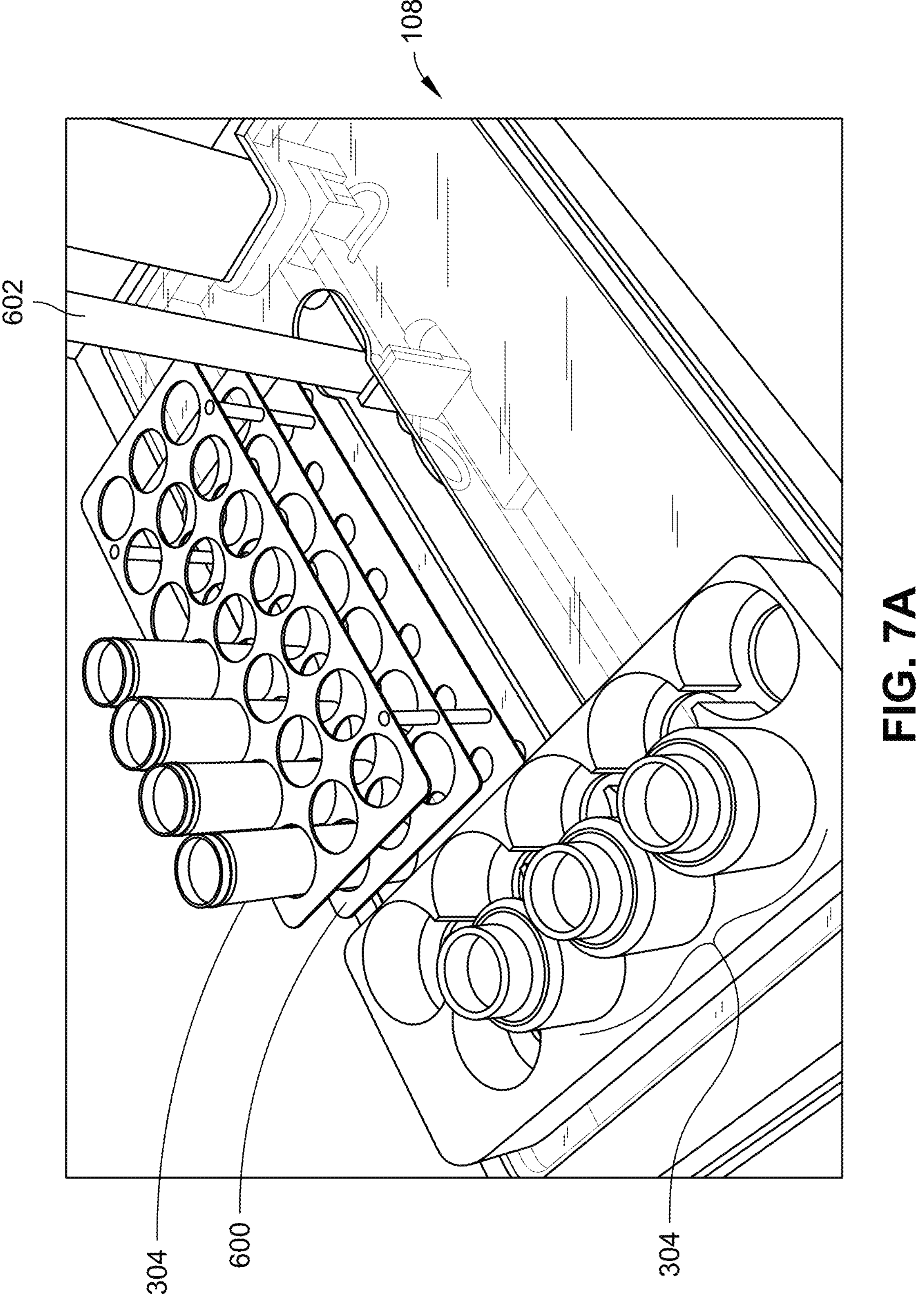
FIG. 7A is an isometric view of example sample containers positioned in sample racks or holders at the sample preparation system.
Figure 7B:
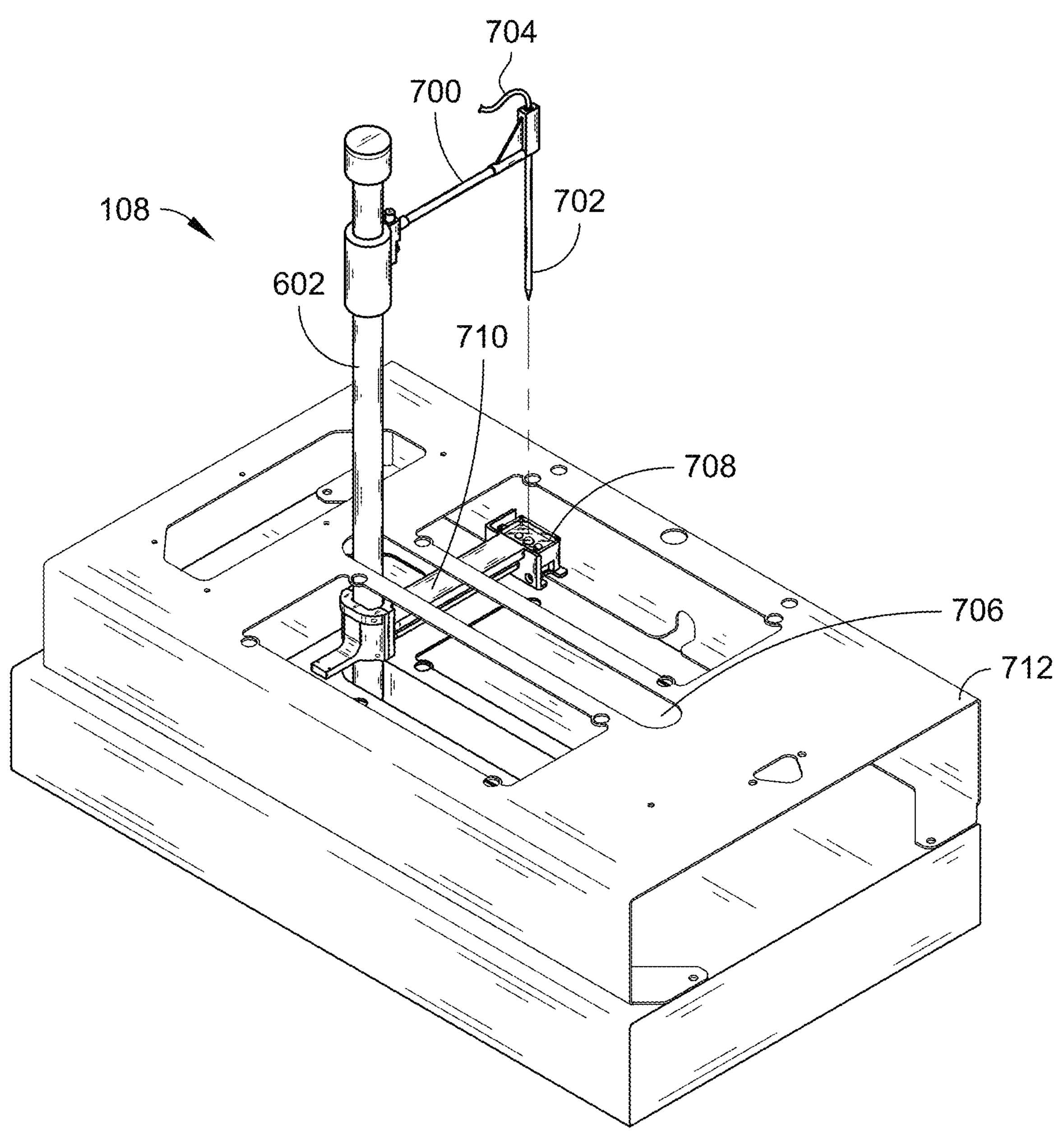
FIG. 7B is an isometric view of a sample preparation system having an identifier capture device to scan unique identifiers on sample containers in accordance with example implementations of the present disclosure.
Figure 7C:
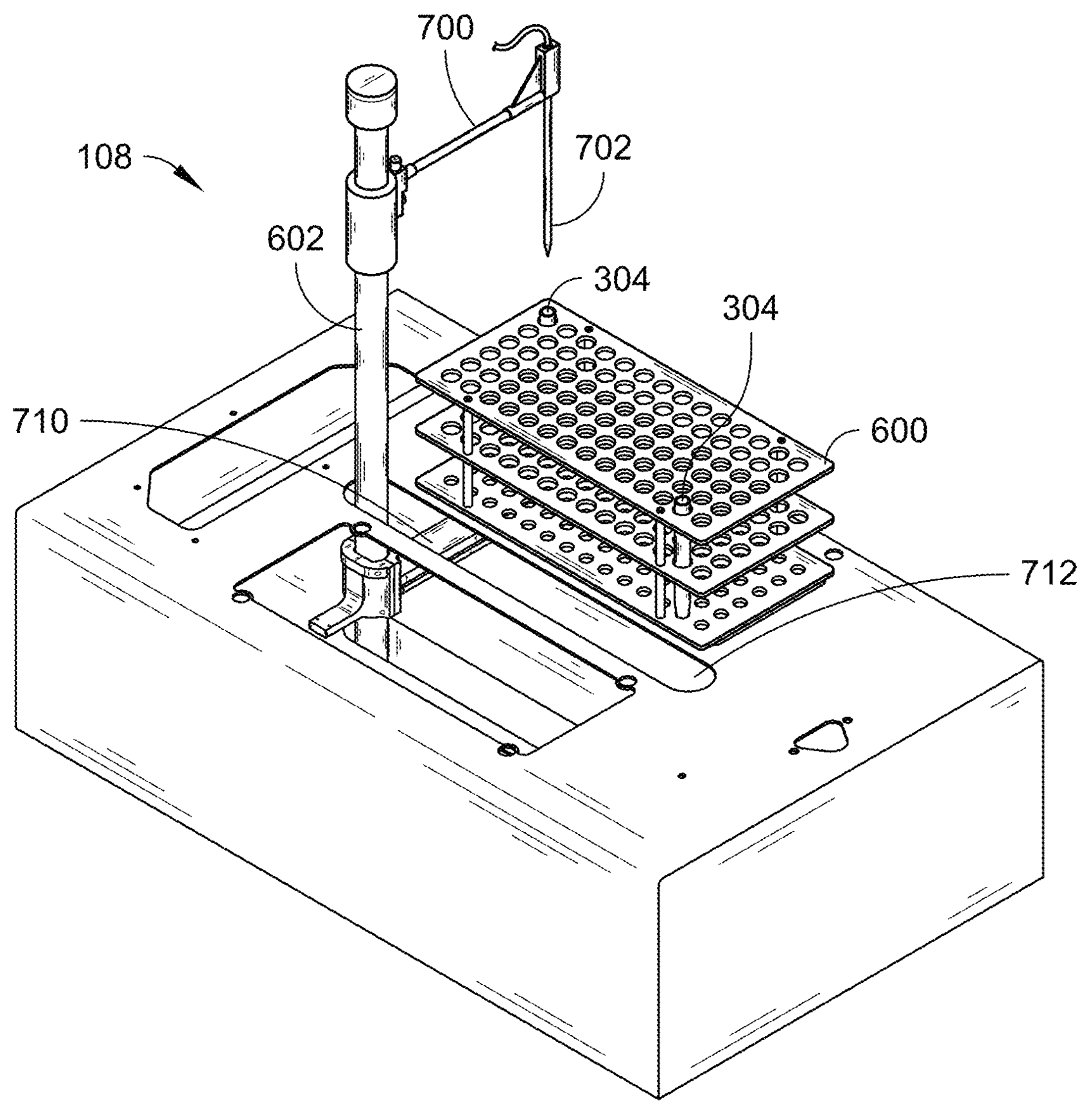
FIG. 7C is an isometric view of a sample preparation system having an identifier capture device to scan unique identifiers on sample containers held by a sample rack in accordance with example implementations of the present disclosure.

Referring to FIG. 7A, example sample holders 600 are shown holding sample containers 304 at the sample preparation system 108 for access by a sample probe supported by support 602. For instance, example sample preparation systems 108 are shown in FIGS. 7B and 7C including identifier capture devices to scan the unique sample identifiers 302 positioned on the sample containers 304 for recognition of types and locations of samples present at the sample preparation system 108. The sample preparation system 108 includes a probe arm assembly 700 coupled to the support 602 to support a sample probe 702 into which a sample or other fluid can be drawn from the sample containers 304 and into tubing 704 or introduced to the sample container 304 through the sample probe 702 (e.g., through pump action, through fluid communication with a vacuum source, or the like). The tubing 704 is coupled to other portions of the sample preparation system 108 to facilitate inline dilution, standard addition, and the like. The support 602 and position of the probe arm assembly 700 are controlled by a motor (not shown), which permits translation of the support 602 through a center slot 706. An identifier capture device 708 is coupled to the support 602 via an identifier arm assembly 710 to permit the identifier capture device 708 to pass beneath a raised surface 712 on which the sample containers 304 are positioned. The identifier capture device 708 passes underneath the raised surface 712 to provide access to the underside of the sample vessels 304 and associated sample identifiers 302. For example, as shown in FIG. 7B, the sample holder 600 can be positioned on the raised surface 712, where the identifier capture device 708 passes underneath to scan the sample identifiers 302 positioned on a bottom surface of the sample containers 304 held in the sample holder 600. The raised surface 712 can define gaps 714 in the surface over which the sample holder 600 and/or sample containers 604 are situated. In this manner, the sample identifiers 302 at the base or bottom of the sample containers 304 are accessible to the identifier capture device 708 when positioned beneath the raised surface 712. Alternatively, the raised surface 712, or a portion thereof, may be constructed from a substantially clear, light transmissive, or transparent material to expose the bottom portion of the sample containers 304 to the identifier capture device 708. Additionally or alternatively, the identifier capture device 708 or additional identifier capture device can be positioned above the raised surface 712 (e.g., mounted to the probe arm assembly 700).

Figure 8:
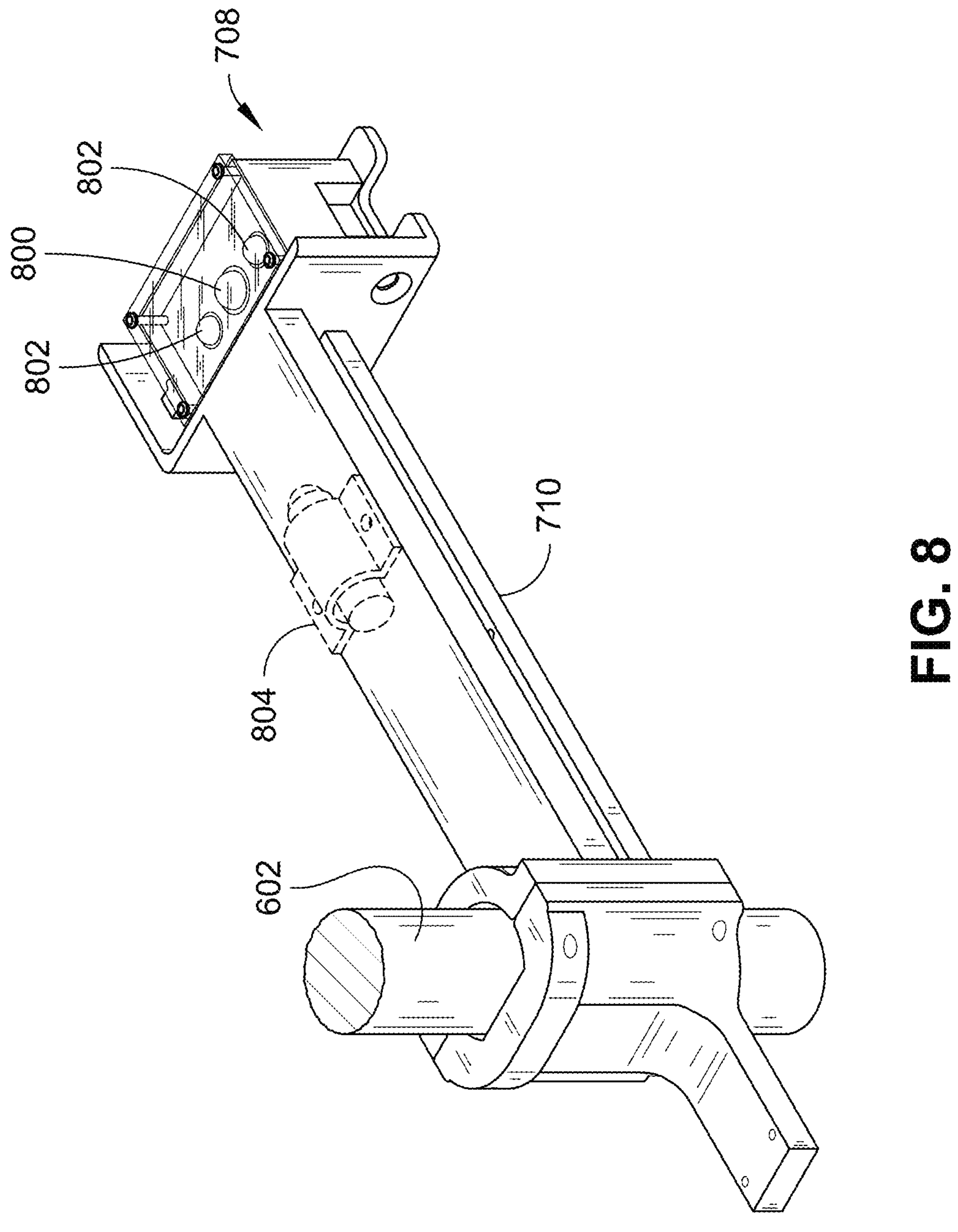
FIG. 8 is an isometric view of an identifier arm assembly of the sample preparation system having an identifier capture device.

The identifier capture device 708 is configured to capture, image, or otherwise recognize the sample identifier 302 as the identifier arm assembly 710 moves the identifier capture device 708 underneath the sample containers 304. For example, as shown in FIG. 8, the identifier capture device 708 includes an imaging device 800 and one or more light sources 802 (e.g., a flash source). In implementations, the imaging device 800 includes a camera or other optical detector configured to capture, image, or otherwise recognize the sample identifier 302 while the imaging device 800 is moving, stationary, or both. For example, the imaging device 800 can capture video images of the sample identifiers 302 and surrounding areas, such that the imaging device 800 can be associated with a display for displaying the captured images, such as on a live or continuous basis. Alternatively or additionally, the imaging device 800 is configured to provide still images of a target, such as the sample identifiers 302. The light source 802 may be configured to illuminate the bottom of the sample containers 304 and/or the sample holders 600 such that the sample identifier 302 has increased visibility to the imaging device 800 during imaging of the sample identifier 302. In an implementation, the identifier capture device 708 is aided by an external light source 804 to provide illumination in addition to or instead of the light source 802. For example, the external light source 804 can be mounted on the identifier arm assembly 710.

Sample Container Discovery

In implementations, the sample preparation system 108 executes a discovery operation to introduce data to the system 100 regarding the positions and identities of samples in the specific rack and vial slots of the sample preparation system 108. An example discovery operation is described with respect to FIGS. 9A and 9B, where six sample containers 304 are held by a first sample holder 600A in positions 1 through 6, respectively. The identifier capture device 708 of the sample preparation system 108 scans the unique sample identifiers 302 positioned on the sample containers 304, where rack/holder and vial information is transmitted to the sample analysis information system 102 for association with the samples identified according to the unique sample identifiers 302. For example, the identifier capture device 708 travels below the raised surface 712 to scan each unique sample identifier 302 positioned on a bottom surface of each sample container 304 through control of the positioning of the identifier capture device 708 along the center slot 706 and the rotation of the identifier capture device 708 by the support 602 and the identifier arm assembly 710. In implementations, the rack/holder and vial information is based on the positioning of the support 602 within the center slot 706 and the position or rotation of the identifier capture device 708 (e.g., relative to an indexing point, relative to the raised surface 712, etc.). For example, when the system 100 identifies the identifier capture device 708 as being positioned under the first sample holder 600A at position 1 (e.g., based on translation and/or rotation from an indexing point), the system 100 can enter rack/holder and vial information to the sample analysis information system 102 attributable to the first sample holder 600A at position 1 as opposed to a second sample holder 600B on an opposite side of the center slot 716 on the raised surface 712 or a different position at the first sample holder 600A.

Figure 9A:
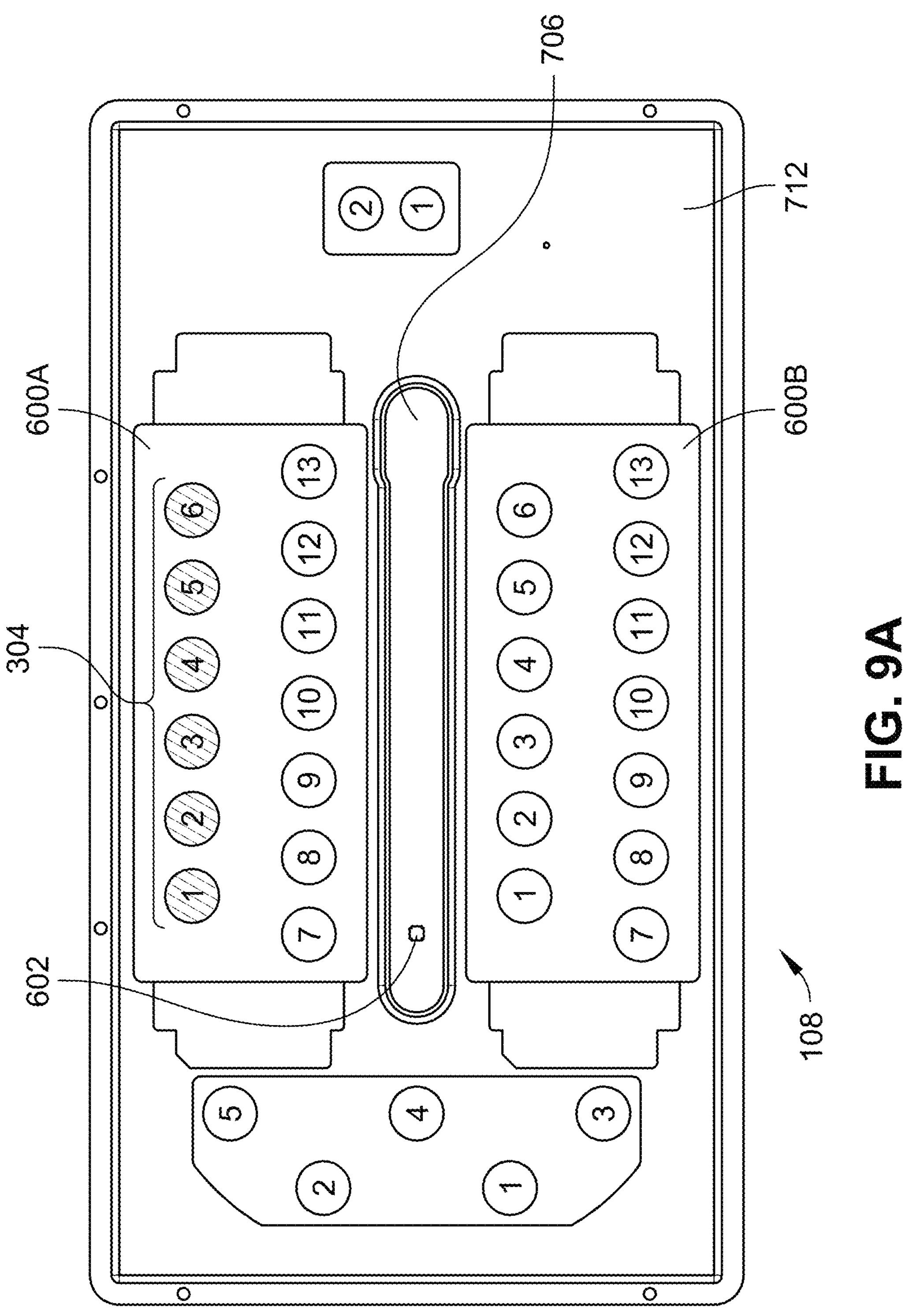
FIG. 9A is an illustration of a user interface of the sample preparation system showing sample containers received in positions 1 through 6 of a sample holder.
Figure 9B:
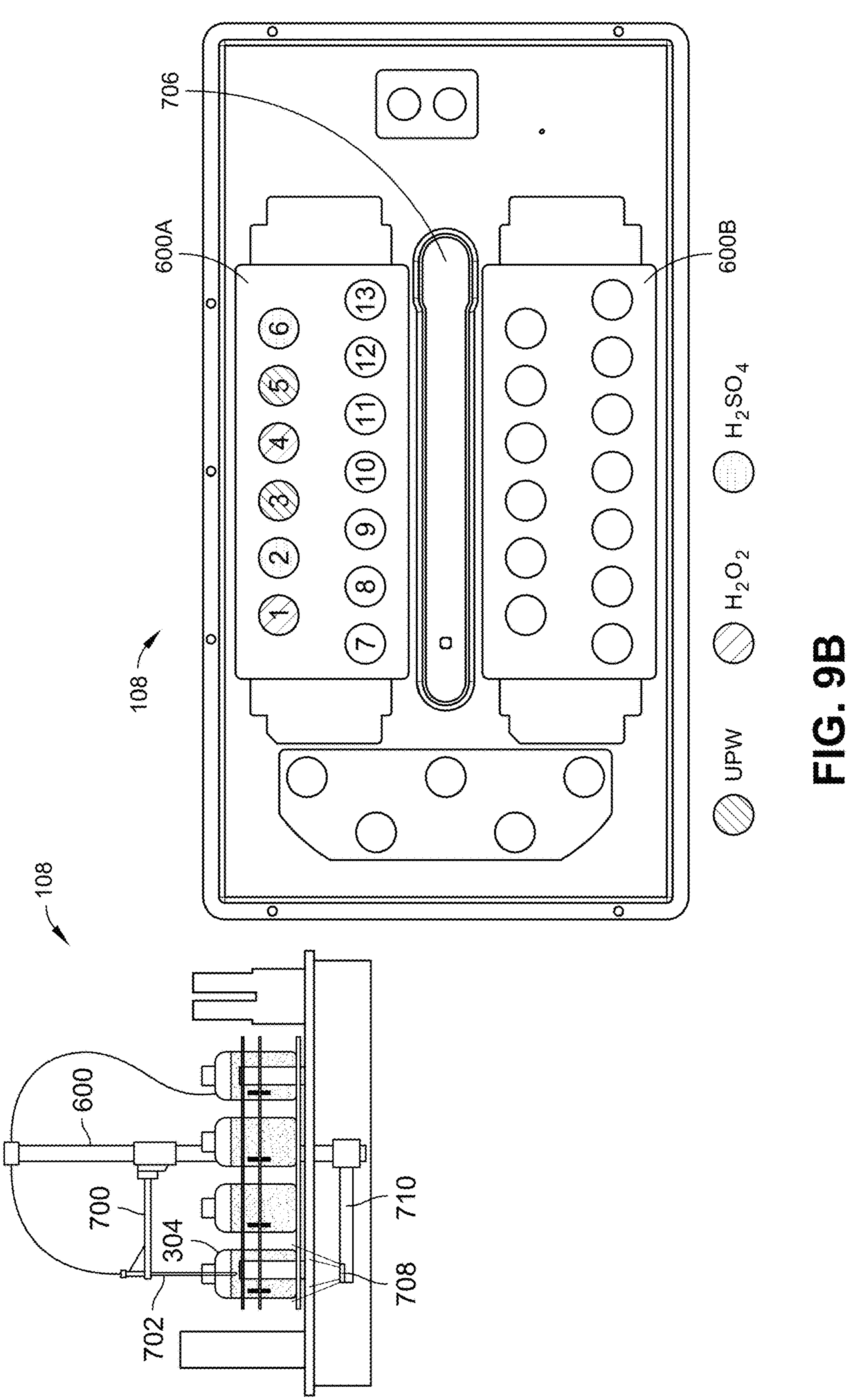
FIG. 9B is an illustration of the sample preparation system undergoing a discover operation to scan the unique identifiers on sample containers and a user interface of the sample preparation system following scanning in accordance with example implementations of the present disclosure.

FIG. 9B shows an example distribution of the sample types held in the first sample holder 600A following the discovery operation. The discovery operation performed by the sample preparation system 108 can result in identification of the specific sample identities present at the specific positions within the sample holders 600 based on the unique sample identifiers 302. For instance, the system 100 can retrieve sample type information and other data associated with the unique sample identifiers 302 as entered through the sample logging manager 106. For example, the system 100 identifies sample identifiers 302 associated with an ultrapure water (UPW) sample type present in positions 3 and 5 of the first sample holder 600A, sample identifiers 302 associated with a hydrogen peroxide ($H_2O_2$) sample type present in positions 1 and 4, and sample identifiers 302 associated with a sulfuric acid ($H_2SO_4$) sample type present in positions 2 and 6. In implementations, the sample preparation system 108 moves the identifier capture device 708 along the positions of the sample containers 304 in a serial manner, however non-serial scanning methods are also contemplated (e.g., tracking of the identifier capture device 708 during scanning to account for positioning during non-serial scanning). In implementations, if no sample identifier 302 is detected in a predefined number of positions of a sample holder (e.g., within one position, within two positions, within three positions, etc.), the sample preparation system 108 directs the identifier capture device 708 to a different sample holder to scan for sample identifiers 302. For instance, if the first two positions of a sample rack 600 are empty, then the sample preparation system 108 skips the remainder of the positions of the sample rack 600, proceeding as though they are empty to perform a faster discovery operation than if the identifier capture device 708 is passed by every position of a sample rack when no sample identifiers 302 are discovered.

Sample Queue Preparation

Following discovery, the system 100 can automatically queue samples for sample preparation and analysis, including introducing fluids to the sample container (e.g., offline or inline), moving sample from one sample container to one or more sample containers (e.g., to provide replicates, archivable samples, etc.), introducing standards at differing dilution factors to build calibration curves for the samples, introducing a wash procedure between different sample types, and the like, based on the information associated with sample types input via the sample data manager 104. For example, the system 100 can queue the identified samples based on the associated sample orders assigned to the sample types of the samples entered via the sample logging manager 106. In implementations, samples having the same sample type are processed sequentially before samples having different sample types. For example, all samples having a sample type of hydrogen fluoride would be processed before samples having a sample type of hydrogen peroxide (based on the previous example of sample order of 1 for hydrogen fluoride and sample order of 2 for hydrogen peroxide). As such, the processing of samples does not require the serial arrangement of samples within the sample holder 600, where the queue can generate a non-serial distribution of sample containers to process. In the example sample configuration of FIG. 9B, the UPW sample type samples would be processed first (e.g., first the sample container at position 3, then the sample container at position 5), then the $H_2O_2$ samples (e.g., first the sample container at position 1, then the sample container at position 4), and then the $H_2SO_4$ samples (e.g., first the sample container at position 2, then the sample container at position 6) in an instance where the priority of sample order assigned by the sample data manager 104 indicates a sample type priority for UPW, then a priority of $H_2O_2$, and then a priority of $H_2SO_4$. The queue includes preparing and analyzing standards for each sample type at varying concentrations to build a calibration curve specific to the sample type for the sample based on the calibration information (e.g., calibration type, number of calibration points, dilution factor for each calibration point, etc.) entered for the sample type via the sample data manager 104.

In implementations, the queue also includes introducing a wash procedure (e.g., to introduce a wash fluid through the fluid lines of the sample preparation system 108, the sample analysis system 110, or combinations thereof) after all samples of a given sample type are processed. For instance, in the example sample configuration of FIG. 9B, a first wash procedure is scheduled after the samples in positions 3 and 5 have both been processed (e.g., including the corresponding standards used to build the respective calibration curves), a second wash procedure is scheduled after the samples in positions 1 and 4 have both been processed, and a third wash procedure is scheduled after the samples in positions 2 and 6 have both been processed. Differing wash procedures can introduce different fluids, have different wash volumes or flow rates, or the like, through valve and pump control of the sample preparation system 108 upon execution of the wash procedure of the sample type protocol.

The discovery operation facilitates discovery of the sample types and their specific rack/vial locations regardless of positioning at the sample preparation system 108. As such, the sample preparation system 108 processes samples according to the identified sample types at their specific rack/vial locations as opposed to being reliant on a serial distribution of samples at the container holder 600. Accordingly, the system 100 coordinates the proper order and sample type protocol for each sample automatically, and without need for the individual placing the samples at the sample preparation system 108 to place the samples in a specific arrangement and without need for the individual to enter a sample type protocol for the samples. In implementations, a manual entry feature is provided for a user to manually enter a sample present at the sample preparation system 108 and associate a sample type with that sample, such as for samples not previously entered into the sample logging manager 106 (e.g., due to scanner malfunction or otherwise). In implementations, the sample data manager 104 can provide a real-time view of the sample queue as determined by the system 100. An example user interface of the sample data manager 104 showing the sample queue is shown with reference to FIG. 10.

As the samples and associated standards are prepared by the sample preparation system 108, they are transferred to the sample analysis system 110 for analytic determination of the contents thereof. The results of the analytic determinations are provided to the sample analysis information system 102, where they are available for review via the sample data manager 104 or other access terminal. In implementations, the results of operation of the sample analysis system 110 are provided to the sample analysis information system 102 in real-time. An example user interface of the sample data manager 104 showing example concentration data of various elements is shown with reference to FIG. 11.

Example Methods for Managing Sample Preparation and Analysis

Figure 12:
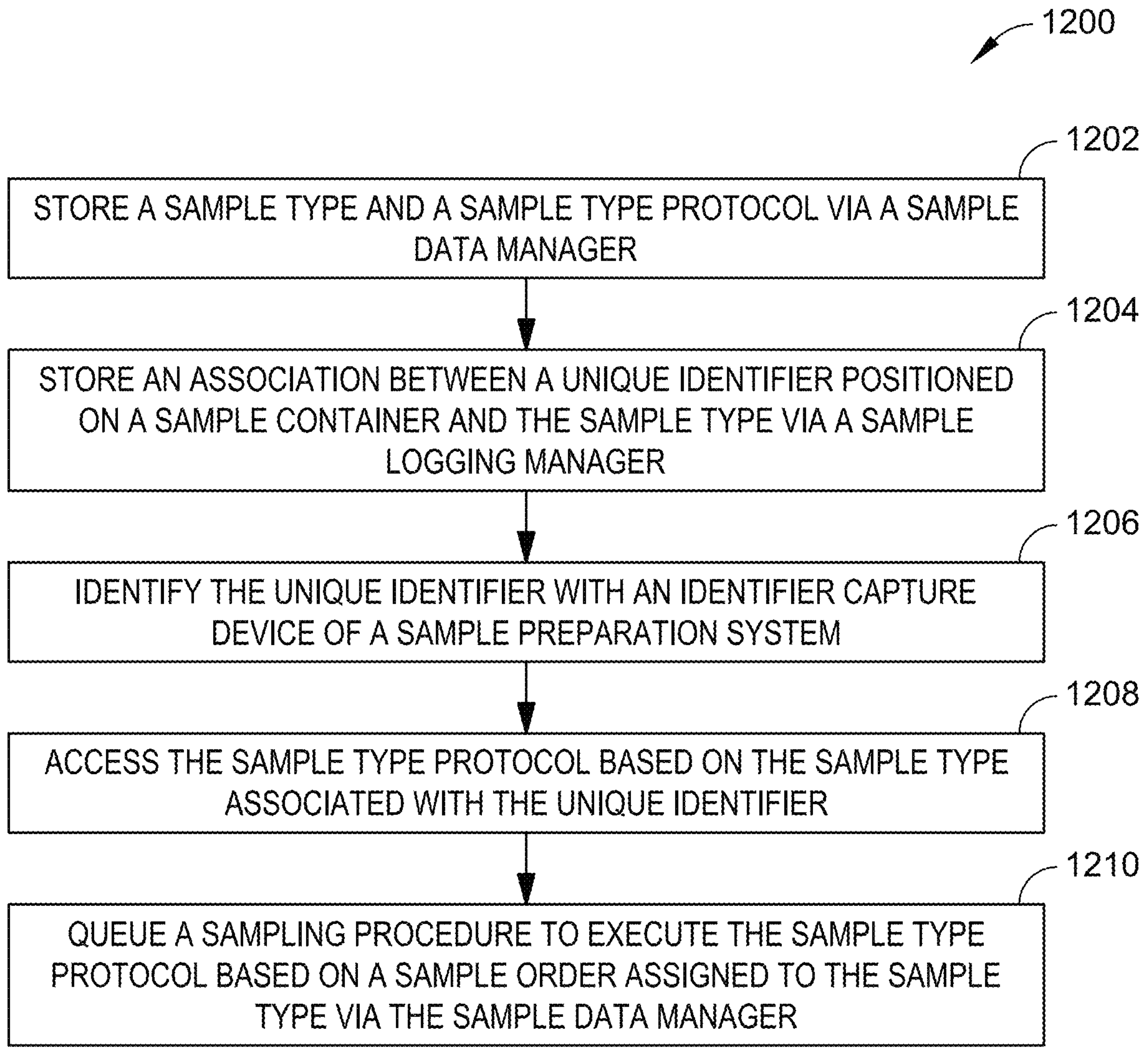
FIG. 12 is a flow diagram of a method for managing data associated with sample preparation and analysis in accordance with example implementations of the present disclosure.

Referring now to FIG. 12, a flow diagram of a method 1200 for managing data associated with sample preparation and analysis is shown in accordance with example implementations of the present disclosure. The method 1200 includes storing a sample type and a sample type protocol via a sample data manager in block 1202. For example, a user with modification authority (e.g., a lab manager) can enter data associated with the sample type and sample type protocol via the sample data manager 104 for storage on the sample analysis information system 102, where the sample type protocol becomes available for execution by the sample preparation system 108. The sample data manager 104 thus facilitates adding or modifying specific sample type protocols for automatic execution by the sample preparation system 108, which can ensure that consistent protocols are utilized by the system 100 to prepare samples for analysis by the sample analysis system 110. The method 1200 also includes storing an association between a unique identifier positioned on a sample container and the sample type via a sample logging manager in block 1204. For example, a user (e.g., a lab technician) can scan a sample identifier 302 on a sample container 304 with the bar code scanner 300 and select via the sample logging manager 106 a sample type (established via the sample data manager 104) to associate the sample type with the specific sample container 304 and corresponding sample identifier 302.

The method 1200 also includes identifying the unique identifier with an identifier capture device of a sample preparation system in block 1206. For example, the sample preparation system 108 scans the sample identifiers 302 on the sample containers 304 with the identifier capture device 708 to identify the unique locations of the sample containers 304 and their corresponding sample identifiers 302 held at the sample preparation system 108 in sample holders 600. The method 1200 also includes accessing the sample type protocol based on the sample type associated with the unique identifier in block 1208. For example, one or more of the sample analysis information system 102, the sample data manager 104, the sample preparation system 108, or other portion of system 100 can access the sample type protocol established by the sample data manager 104 for the unique identifier 302 identified by the sample preparation system 108 based on the sample type assigned to the unique identifier 302 via the sample logging manager 106. The method 1200 also includes queuing a sampling procedure to execute the sample type protocol based on a sample order assigned to the sample type via the sample data manager in block 1210. For example, one or more of the sample analysis information system 102, the sample data manager 104, the sample preparation system 108, or other portion of system 100 can execute the sample type protocol established via the sample data manager 104 for each sample identified at the sample preparation system 108 based on a sample order assigned to the particular sample type via the sample data manager 104. The sample type protocol can include, for example, preparing and analyzing a plurality of standard solutions to build a calibration curve for each sample, executing a washing procedure following completion of analysis of a group of the same sample types present at the sample preparation system 108, and the like.

Figure 13:
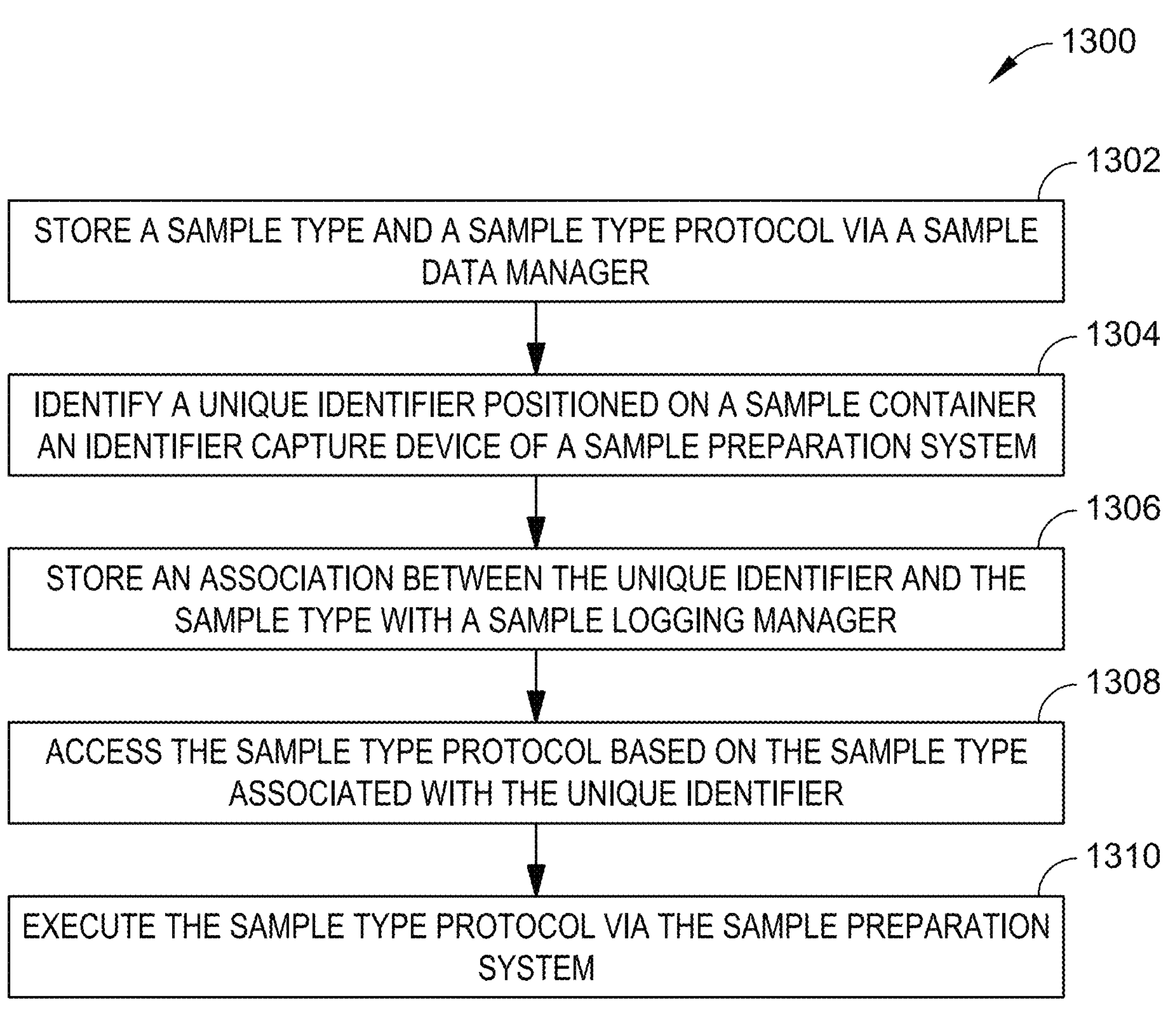
FIG. 13 is a flow diagram of a method for managing data associated with sample preparation and analysis in accordance with example implementations of the present disclosure.

Referring now to FIG. 13, a flow diagram of a method 1300 for managing data associated with sample preparation and analysis is shown in accordance with example implementations of the present disclosure. The method 1300 includes storing a sample type and a sample type protocol via a sample data manager in block 1302. For example, a user with modification authority (e.g., a lab manager) can enter data associated with the sample type and sample type protocol via the sample data manager 104 for storage on the sample analysis information system 102, where the sample type protocol becomes available for execution by the sample preparation system 108. The sample data manager 104 thus facilitates adding or modifying specific sample type protocols for automatic execution by the sample preparation system 108, which can ensure that consistent protocols are utilized by the system 100 to prepare samples for analysis by the sample analysis system 110. The method 1300 also includes identifying a unique identifier positioned on a sample container with an identifier capture device of the sample preparation system in block 1304. For example, the sample preparation system 108 scans the sample identifiers 302 on the sample containers 304 (e.g., with the identifier capture device 708, with a scanner of the mass balance 500, etc.) to identify sample present at the sample preparation system 108, or a lack of identified samples present at the sample preparation system 108.

The method 1300 also includes storing an association between the unique identifier positioned on the sample container and the sample type via a sample logging manager in block 1306. For example, a user (e.g., a lab technician) can scan a sample identifier 302 on a sample container 304 (e.g., with the bar code scanner 300, with the identifier capture device 708, with a scanner of the mass balance 500, etc.) and select via the sample logging manager 106 a sample type (established via the sample data manager 104) to associate the sample type with the specific sample container 304 and corresponding sample identifier 302.

The method 1300 also includes accessing the sample type protocol based on the sample type associated with the unique identifier in block 1308. For example, one or more of the sample analysis information system 102, the sample data manager 104, the sample preparation system 108, or other portion of system 100 can access the sample type protocol established by the sample data manager 104 for the unique identifier 302 identified by the sample preparation system 108 based on the sample type assigned to the unique identifier 302 via the sample logging manager 106. The method 1300 also includes executing the sample type protocol via the sample preparation system in block 1310. For example, the sample preparation system 108 can execute the sample type protocol accessed via the sample analysis information system and established via the sample data manager 104 for each sample identified at the sample preparation system 108 to prepare samples for analysis or facilitate their preparation for future analysis. The sample type protocol can include, for example, introducing fluids to the sample container (e.g., offline or inline), moving sample from one sample container to one or more sample containers (e.g., to provide replicates, archivable samples, etc.), introducing standards at differing dilution factors to build calibration curves for the samples, introducing a wash procedure between different sample types, and the like, based on the information associated with sample types input via the sample data manager 104.

Sample Container Status Tracking

The system 100 can also facilitate tracking of sample containers 304 through a facility or group of facilities. The unique identifiers 302 on the sample containers 304 can be used to track data associated with each sample container 304 through scanning of the unique identifiers (e.g., via the bar code scanner 300 or other device) during various portions of the cycle of use of the sample container and storage and access of the data via the sample analysis information system 102 or other portion of the system 100. For instance, the data associated with each sample container 304 can include, but is not limited to, a current status of the sample container, a location of the sample container, a sample type currently held in the sample container, a concentration of analyte currently held in the sample container, a history of samples types held in the sample container, a history of concentration of analytes held in the sample container, and the like.

The status of a sample container 304 is dependent on the particular portion of the cycle of use of the sample container 304 and can include, but is not limited to, an available status, a carry out status, a receiving status, an analysis status, a completed status, a cleaning status, and a verification status. The available status can refer to a sample container 304 being stored in a cleaned state, ready to be used for holding a sample. For example, a user can utilize the sample logging manager 106 and the bar code scanner 300 or other device to scan the sample identifier 302 of the sample container 304 and input the available status to be associated with the particular sample identifier 302 (e.g., stored at the sample analysis information system 102). In implementations, the sample container statuses available for selection via the sample logging manager 106 are input into the system 100 via the sample data manager 104 interface.

The carry out status can refer to removal of the sample container 304 from storage for collection of a particular sample in the sample container 304. For example, a user can utilize the sample logging manager 106 and the bar code scanner 300 or other device to scan the sample identifier 302 of the sample container 304 and input the carry out status to be associated with the particular sample identifier 302 following removal from storage. Once a sample is introduced to the sample container 304, a user can transfer the sample container 304 to a laboratory or other location for analysis of the sample. The receiving status can refer to receipt of the sample container 304 in the laboratory or other location, prior to analysis of the sample held in the sample container 304 (e.g., the sample is awaiting analysis). For example, a user can utilize the sample logging manager 106 and the bar code scanner 300 or other device to scan the sample identifier 302 of the sample container 304 and input the receiving status to be associated with the particular sample identifier 302 following transfer of the sample container 304 to the laboratory or other location for analysis.

The analysis status can refer to processing of the sample for analysis. For example, the sample preparation system 108 can scan the sample identifier 302 (e.g., during the discovery operation described herein) and upload the analysis status to the sample analysis information system 102. Alternatively or additionally, a user can utilize the sample logging manager 106 and the bar code scanner 300 or other device to scan the sample identifier 302 of the sample container 304 while placing the sample container at the sample preparation device 108 (e.g., in the sample holder 600). The completed status can refer to analysis of the sample by the sample analysis system 110 being complete. For example, the sample analysis system 110 can upload the completed status to the sample analysis information system 102 once concentration data of the analytes of interest of the sample are provided to the sample analysis information system 102, the sample data manager 104, or other portion of system 100.

The cleaning status can refer to washing the sample container 304 to remove residual contaminants or residual sample following analysis of the sample. For example, a user can utilize the sample logging manager 106 and the bar code scanner 300 or other device to scan the sample identifier 302 of the sample container 304 and input the cleaning status to be associated with the particular sample identifier 302 following analysis of the sample from the sample container 304. Additionally or alternatively, a wash station can include a bar code scanner 300, an identifier capture device 708, or other scanning device to automatically scan the sample identifier 302 when received for cleaning, during cleaning, following cleaning, or the like, to associate the cleaning status with the sample identifier 302 for access at the sample analysis information system 102. Following cleaning, a sample container 304 can be introduced to storage, where the sample identifier 302 can be associated with the available status, or the sample container 304 can be transferred to a sample preparation system 108 to prepare a sample from the sample container 304 for analysis by the sample analysis system 110 to analytically verify the cleanliness of the sample container 304. For example, the sample preparation system 108 can scan the sample identifier 302 (e.g., during the discovery operation described herein) and upload the verification status to the sample analysis information system 102. Alternatively or additionally, a user can utilize the sample logging manager 106 and the bar code scanner 300 or other device to scan the sample identifier 302 of the sample container 304 while placing the sample container at the sample preparation device 108 (e.g., in the sample holder 600) for verification.

Computer System Implementation

Aspects of the system 100 described herein are executed in a computer system. For example, one or more components of the sample analysis information system 102, the sample data manager 104, the sample logging manager 106, the sample preparation system 108, and the sample analysis system 110 include a computing device, communicate with a computing device through a network, or both, to facilitate aspects of the disclosure described herein. For example, one or more components of the sample analysis information system 102, the sample data manager 104, the sample logging manager 106, the sample preparation system 108, and the sample analysis system 110 can include a computer controller or are operably coupled with a computer controller to execute the operations described herein. For example, the system 100 can include a computing device having a processor and memory or communicatively coupled with a processor and/or memory. The processor provides processing functionality for the computing device and may include any number of processors, micro-controllers, or other processing systems, and resident or external memory for storing data and other information accessed or generated by the computing device. The processor may execute one or more software programs that implement the techniques described herein. The processor is not limited by the materials from which it is formed or the processing mechanisms employed therein and, as such, may be implemented via semiconductor(s) and/or transistors (e.g., electronic integrated circuits (ICs)), and so forth.

Memory accessible by the controller is an example of device-readable storage media that provides storage functionality to store various data associated with the operation of the computing device, such as software programs or code segments, or other data to instruct the processor and other elements of the computing device to perform the techniques described herein. A wide variety of types and combinations of memory may be employed. The memory may be integral with the processor, stand-alone memory, or a combination of both. The memory may include, for example, removable and non-removable memory elements such as RAM, ROM, Flash (e.g., SD Card, mini-SD card, micro-SD Card), magnetic, optical, USB memory devices, and so forth. In embodiments of the computing device, the memory may include removable ICC (Integrated Circuit Card) memory such as provided by SIM (Subscriber Identity Module) cards, USIM (Universal Subscriber Identity Module) cards, UICC (Universal Integrated Circuit Cards), and so on.

The computing device includes a display to display information to a user of the computing device. In embodiments, the display may comprise a CRT (Cathode Ray Tube) display, an LED (Light Emitting Diode) display, an OLED (Organic LED) display, an LCD (Liquid Crystal Diode) display, a TFT (Thin Film Transistor) LCD display, an LEP (Light Emitting Polymer) or PLED (Polymer Light Emitting Diode) display, and so forth, configured to display text and/or graphical information such as a graphical user interface. The display may be backlit via a backlight such that it may be viewed in the dark or other low-light environments. The display may be provided with a touch screen to receive input (e.g., data, commands, etc.) from a user. For example, a user may operate the computing device by touching the touch screen and/or by performing gestures on the touch screen. In some embodiments, the touch screen may be a capacitive touch screen, a resistive touch screen, an infrared touch screen, combinations thereof, and the like. The computing device may further include one or more input/output (I/O) devices (e.g., a keypad, buttons, a wireless input device, a thumbwheel input device, a trackstick input device, and so on). The I/O devices may include one or more audio I/O devices, such as a microphone, speakers, and so on. The user interface may provide functionality to allow the user to interact with one or more applications of the computing device by providing inputs (e.g., sample identities, sample locations, sample type protocols, sample rack type, fluid flow rates, analysis system operation, valve timing, pump timing, etc.) via the touch screen and/or the I/O devices. For example, the user interface may cause an application programming interface (API) to be generated to expose functionality to a sample analysis information system controller to allow the user to interact with an application by providing inputs via the touch screen and/or the I/O devices to provide desired sample throughput or sample preparation and subsequent analysis.

The computing system may also include a communication interface to transfer of data or control instructions between different devices (e.g., components/peripherals) and/or over one or more networks. The communication interface may include a variety of communication components and functionality including, but not necessarily limited to: a browser; a transmitter and/or receiver; data ports; software interfaces and drivers; networking interfaces; data processing components; and so forth.

The one or more networks are representative of a variety of different communication pathways and network connections which may be employed, individually or in combinations, to communicate among the components of the system 100. Thus, the one or more networks may be representative of communication pathways achieved using a single network or multiple networks. Further, the one or more networks are representative of a variety of different types of networks and connections that are contemplated including, but not necessarily limited to: the Internet; an intranet; a Personal Area Network (PAN); a Local Area Network (LAN) (e.g., Ethernet); a Wide Area Network (WAN); a satellite network; a cellular network; a mobile data network; wired and/or wireless connections; and so forth. Examples of wireless networks include, but are not necessarily limited to: networks configured for communications according to: one or more standard of the Institute of Electrical and Electronics Engineers (IEEE), such as 802.11 or 802.16 (Wi-Max) standards; Wi-Fi standards promulgated by the Wi-Fi Alliance; Bluetooth standards promulgated by the Bluetooth Special Interest Group; and so on. Wired communications are also contemplated such as through Universal Serial Bus (USB), Ethernet, serial connections, and so forth.

Although particular embodiments of this invention have been illustrated, it is apparent that various modifications and embodiments of the invention may be made by those skilled in the art without departing from the scope and spirit of the foregoing disclosure. Accordingly, the scope of the invention should be limited only by the claims appended hereto.

While the subject matter has been described in language specific to structural features and/or process operations, it is to be understood that the subject matter defined in the appended claims is not necessarily limited to the specific features or acts described above. Rather, the specific features and acts described above are disclosed as example forms of implementing the claims.

What is claimed is:

1. A sample and standard preparation system, comprising: storage media storing computer-readable instructions and a sample analysis information system, the sample and standard preparation system further comprising, and the sample analysis information system communicatively connected with, each of:

a sample data manager comprising a part of the instructions, a sample logging manager comprising a part of the instructions, and a sample preparation system comprising a part of the instructions and further including:

a sample probe, an identifier capture device comprising a part of the instructions configured to identify a unique identifier positioned on a sample container, a support coupled to each of the sample probe and the identifier capture device, and a slot formed in a surface supporting the sample container, the support configured to translate through the slot to move each of the sample probe and the identifier capture device relative to the sample container;

wherein:

(i) the sample data manager instructions are configured to store on the sample analysis information system a sample type with a sample type protocol, (ii) the sample logging manager instructions are configured to assign the sample type stored on the sample analysis information system with the unique identifier positioned on the sample container, (iii) the sample preparation system includes the identifier capture device at a first location, and the identifier capture device instructions are configured to identify the unique identifier and to store on the sample analysis information system an association between a unique location of the sample container and the unique identifier where the sample container is located, the unique location of the sample container corresponding to a position of the support within the slot and a position of the identifier capture device relative to an indexing point when identifying the unique identifier, and (iv) the sample preparation system instructions are configured to access the sample type protocol from the sample analysis information system and to execute the sample type protocol responsive to a queue associated with a sample order assigned to the sample type via the sample data manager; and wherein the sample probe is configured to, without removing the sample container from the unique location or the first location, at least one of:

(i) transfer sample from the sample container to one or more additional sample containers responsive to execution of the sample type protocol, or (ii) introduce one or more additional fluids to the sample container responsive to execution of the sample type protocol.

2. The sample and standard preparation system of claim 1, wherein the sample preparation system includes a unique location for each individual sample container, and wherein the identifier capture device instructions are configured to scan each unique location and associate with the sample analysis information system each unique location.

3. The sample and standard preparation system of claim 2, wherein the sample analysis information system instructions are configured to assign the queue based on the sample order and the unique location associated by the identifier capture device with the unique identifier positioned on the sample container.

4. The sample and standard preparation system of claim 2, wherein the sample preparation system instructions are configured to prepare sample types having sample orders with a higher priority before sample types having sample orders with a lower priority.

5. The sample and standard preparation system of claim 2, wherein the queue is based on a non-serial distribution of unique locations of sample containers at the sample preparation system.

6. The sample and standard preparation system of claim 5, wherein the identifier capture device instructions are configured to scan each unique location in a serial manner.

7. The sample and standard preparation system of claim 6, wherein the sample and standard preparation system further comprises a sample analysis system and wherein the sample type protocol includes an analysis protocol accessible by the sample analysis system, wherein the analysis protocol includes at least one of a list of analytes to be analyzed by the sample analysis system, calibration levels for each standard calibration for each analyte to be analyzed by the sample analysis system, and dilution factors for each standard calibration for each analyte to be analyzed by the sample analysis system.

8. The sample and standard preparation system of claim 1, wherein the sample type protocol includes data associated with at least one of a dilution factor specific to the sample type, a calibration type specific to the sample type, a number of calibration points specific to the sample type, and a dilution factor associated with a calibration point specific to the sample type.

9. The sample and standard preparation system of claim 1, wherein the sample and standard preparation system further comprises a sample analysis system and wherein the sample analysis information system is further communicatively connected with the sample analysis system, the sample analysis system configured to receive a sample from the sample preparation system and determine a concentration of one or more analytes of interest in the sample.

10. The sample and standard preparation system of claim 1, wherein the sample analysis information system instructions are configured to store data associated with the sample container based on the unique identifier.

11. The sample and standard preparation system of claim 10, wherein the data associated with the sample container includes at least one of a current status of the sample container, a location of the sample container, a sample type currently held in the sample container, a concentration of analyte currently held in the sample container, a history of samples types held in the sample container, and a history of concentration of analytes held in the sample container.

12. The sample and standard preparation system of claim 1, wherein the sample analysis information system includes a database configured to store one or more of the sample type protocol, the unique identifier, and the sample order.

13. The sample and standard preparation system of claim 1, wherein the sample preparation system includes a mass balance configured to measure a weight of sample held within the sample container.

14. The sample and standard preparation system of claim 13, wherein the sample type protocol includes a minimum weight of sample and a maximum weight of sample.

15. The sample and standard preparation system of claim 14, wherein the sample preparation system includes a display, and wherein the sample preparation system instructions are configured to display a current weight of sample held on the mass balance on the display in a first format when the current weight is below the minimum weight of sample or above the maximum weight of sample and to display the current weight of sample held on the mass balance on the display in a second format when the current weight is at the minimum weight of sample, between the minimum weight of sample and the maximum weight of sample, or at the maximum weight of sample, responsive to execution of the sample type protocol.

16. The sample and standard preparation system of claim 13, wherein the mass balance includes a scanner configured to identify the unique identifier positioned on the sample container.

17. A sample and standard preparation system, comprising:

storage media storing computer-readable instructions, and a sample analysis information system, the sample and standard preparation system further comprising, and the sample analysis information system communicatively connected with, each of:

a sample data manager comprising a part of the instructions, a sample logging manager comprising a part of the instructions, and a sample preparation system comprising a part of the instructions and further including:

a sample probe, an identifier capture device comprising a part of the instructions configured to identify a unique identifier positioned on a sample container, a support coupled to each of the sample probe and the identifier capture device, and a slot formed in a surface supporting the sample container, the support configured to translate through the slot to move each of the sample probe and the identifier capture device relative to the sample container;

wherein:

(i) the sample data manager instructions are configured to store on the sample analysis information system a sample type with a sample type protocol, (ii) the sample logging manager instructions are configured to assign the sample type stored on the sample analysis information system with the unique identifier positioned on the sample container, (iii) the sample preparation system includes the identifier capture device at a first location, and the identifier capture device instructions are configured to identify the unique identifier and to store on the sample analysis information system an association between a unique location of the sample container and the unique identifier where the sample container is located, the unique location of the sample container corresponding to a position of the support within the slot and a position of the identifier capture device relative to an indexing point when identifying the unique identifier, and (iv) the sample preparation system instructions are configured to access the sample type protocol from the sample analysis information system and to execute the sample type protocol responsive to a queue associated with a sample order assigned to the sample type via the sample data manager.

* * * * *